United States Patent
Meadows et al.

(10) Patent No.: US 11,207,301 B2
(45) Date of Patent: Dec. 28, 2021

(54) SPHINGOSINE 1 PHOSPHATE RECEPTOR AGONISTS FOR NEUROPROTECTION

(71) Applicant: RECEPTOS LLC, New York, NY (US)

(72) Inventors: Kristen R. Taylor Meadows, San Diego, CA (US); Brett Skolnick, San Diego, CA (US); Deepak Dalvie, Carlsbad, CA (US)

(73) Assignee: RECEPTOS LLC, New York, NY (US)

( * ) Notice: Subject to any disclaimer, the term of this patent is extended or adjusted under 35 U.S.C. 154(b) by 10 days.

(21) Appl. No.: 16/611,451

(22) PCT Filed: May 8, 2018

(86) PCT No.: PCT/US2018/031695
§ 371 (c)(1),
(2) Date: Nov. 6, 2019

(87) PCT Pub. No.: WO2018/208855
PCT Pub. Date: Nov. 15, 2018

(65) Prior Publication Data
US 2020/0085795 A1    Mar. 19, 2020

Related U.S. Application Data

(60) Provisional application No. 62/502,909, filed on May 8, 2017, provisional application No. 62/544,467, filed on Aug. 11, 2017.

(51) Int. Cl.
*A61K 31/4245* (2006.01)
(52) U.S. Cl.
CPC ................ *A61K 31/4245* (2013.01)
(58) Field of Classification Search
CPC ................ C07D 271/06; A61K 31/4245
See application file for complete search history.

(56) References Cited

U.S. PATENT DOCUMENTS

| 10,239,846 B2 * | 3/2019 | Martinborough | ....... A61P 43/00 |
| 2011/0172202 A1 | 7/2011 | Martinborough et al. | |

FOREIGN PATENT DOCUMENTS

EP    2366702    9/2011

OTHER PUBLICATIONS

Conference Paper in Alzheimer's & dementia: the journal of the Alzheimer's Association Jul. 2014 to Elizabeth van der kam et al.*
Anonymous, "NCT02294058: A Phase 3, Multi-Center, Randomized, Double-Blind, Double Dummy, Active Controlled, Parallel Group Study to Evaluate the Efficacy and Safety of RPC 1063 Administered Orally to Relapsing Multiple Sclerosis Patients", May 4, 2017.
Deogracias et al., "Fingolimod, a sphingosine-1 phosphate receptor modulator, increases BDNF levels and improves symptoms of a mouse model of Rett syndrome", vol. 109, No. 35, Aug. 28, 2012, pp. 14230-14235.
Scott et al., "Ozanimod (RCP1063) is apotent sphingosine-1-phosphate receptor-1 ($S1P_1$) and receptor-5 ($S1P_5$) agonist with autoimmune disease-modifying activity", vol. 173, 2016, pp. 1778-1792.

* cited by examiner

*Primary Examiner* — Kamal A Saeed
(74) *Attorney, Agent, or Firm* — Seed IP Law Group LLP

(57) ABSTRACT

Methods of treating conditions for which S1P-mediated neuroprotection is medically indicated, comprising administering to a subject in need thereof an agonist of the sphingosine 1-phosphate receptor (S1P receptor); such as a compound having the following structure (See Formula 1): or a pharmaceutically acceptable salt, stereoisomer, homolog, hydrate or solvate thereof.

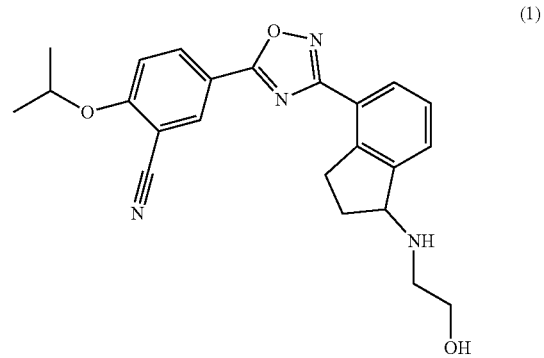

(1)

12 Claims, 15 Drawing Sheets

| Compounds | IC$_{50}$ Against MAO-A; Inhibition of the formation of 4-hydoxy-quinoline (μM) | IC$_{50}$ Against MAO-B; Inhibition of the formation of 4-hydoxy-quinoline (μM) |
|---|---|---|
| Compound 2-S | 1.2 | 0.032 |
| Compound 1 | No inhibition | 0.0066 |

FIG. 4

|  | Lot | EC$_{50}$ (nM) AKT Phosphorylation | | EC$_{50}$ (nM) ERK Phosphorylation | |
| --- | --- | --- | --- | --- | --- |
|  |  | Mean | SEM | Mean | SEM |
| ozanimod | 24 | 2.03 | 0.62 | 0.80 | 0.30 |
| Cmp 3 | 8 | 0.23 | 0.08 | 0.11 | 0.06 |
| Cmp 1 | 2 | 0.66 | 0.18 | 0.29 | 0.15 |
| FTY720-p | 4752227-21 | 0.17 | 0.09 | 0.16 | 0.15 |

FIG. 7

| Test Compound | Lot | EC$_{50}$ (nM) AKT Phosphorylation Mean ± SEM | | EC$_{50}$ (nM) ERK Phosphorylation Mean ± SEM | |
|---|---|---|---|---|---|
| | | Mouse | Human | Mouse | Human |
| ozanimod | 24 | 0.90 ± 0.43 | ND | 2.42 ± 1.30 | 1.93 ± 0.66 |
| Cmp 3 | 8 | 0.13 ± 0.06 | ND | 0.23 ± 0.05 | 0.50 ± 0.15 |
| Cmp 1 | 2 | 0.49 ± 0.22 | ND | 0.87 ± 0.34 | 2.12 ± 0.84 |
| FTY720-p | 4752227-21 | 0.09 ± 0.01 | ND | 0.14 ± 0.05 | 0.63 ± 0.26 |

FIG. 10

SPHINGOSINE 1 PHOSPHATE RECEPTOR AGONISTS FOR NEUROPROTECTION

FIELD OF THE INVENTION

The invention relates to methods of treating conditions for which S1P receptor-mediated neuroprotection is medically indicated, comprising administering to a subject in need thereof an agonist of the sphingosine 1-phosphate receptor (S1P receptor).

BACKGROUND

The $S1P_1/EDG_1$ receptor is a G-protein coupled receptor (GPCR) and is a member of the endothelial cell differentiation gene (EDG) receptor family. Endogenous ligands for EDG receptors include lysophospholipids, such as sphingosine-1-phosphate (S1P). Like all GPCRs, ligation of the receptor propagates second messenger signals via activation of G-proteins (alpha, beta and gamma).

Development of small molecule $S1P_1$ agonists has provided insight into some physiological roles of the $S1P_1/S1P$-receptor signaling system. Agonism of the $S1P_1$ receptor perturbs lymphocyte trafficking, sequestering them in lymph nodes and other secondary lymphoid tissue. This leads to rapid and reversible lymphopenia, and is probably due to receptor ligation on both lymphatic endothelial cells and lymphocytes themselves (Rosen et al, Immunol. Rev., 195: 160-177, 2003). A clinically valuable consequence of lymphocyte sequestration is exclusion of them from sights of inflammation and/or auto-immune reactivity in peripheral tissues. This activity has led to development of $S1P_1$ agonists for treating inflammatory and autoimmune conditions of the central nervous system.

SUMMARY OF THE INVENTION

The invention relates to methods of treating conditions for which S1P receptor-mediated neuroprotection is medically indicated, comprising administering to a subject in need thereof an agonist of the sphingosine 1-phosphate receptor (S1P). In a specific embodiment, the S1P receptor agonist is a S1P receptor subtype 1 ($S1P_1$) agonist. In a more specific embodiment, the $S1P_1$ agonist is ozanimod, and in other embodiments has a structure as disclosed below, or a pharmaceutically acceptable salt, stereoisomer, homolog, hydrate or solvate thereof.

In further embodiments, the S1P-mediated neuroprotection is associated with reduction in spinal cord inflammation and/or demyelination in the context of, for example, multiple sclerosis, as well as reduction in T cell expansion, a decrease in monocyte infiltration into the spinal cord, and/or limiting microglia expansion into the spinal cord. To this end, the compounds disclosed herein would have benefit in providing neuroprotection in the context of the following disease indications: Parkinson's disease, Huntington disease, amyotrophic lateral sclerosis, Alzheimer's disease, multiple sclerosis (primary progressive and/or secondary progressive), Rett syndrome, and muscular dystrophy.

In yet a further embodiment, the S1P receptor-mediated neuroprotection is associated with reduction of brain volume loss, for example in the context of treatment for relapsing multiple sclerosis. Brain volume loss correlates with, and is predictive for, disability associated with relapsing multiple sclerosis.

In yet a further embodiment, the the S1P receptor-mediated neuroprotection is associated with reduction of mono- amino oxidase B (MAO-B) activity, for example in the context of treatment for Alzheimer's disease or Parkinson's disease.

In yet another embodiment, the S1P receptor-mediated neuroprotection is associated with increased AKT and/or ERK activity in cortical astrocytes.

These and other aspects of this invention will be evident upon review of the following detailed description.

BRIEF DESCRIPTION OF THE DRAWINGS

FIG. 4 is a table showing the $IC_{50}$ of Compound 1 and Compound 2-S against MAO-A and MAO-B as measured by the inhibition of formation of 4-hydroxyquinoline from kynuramine.

FIG. 7 shows $EC_{50}$ values for AKT and ERK phosphorylation in primary rat astrocytes with ozanimod, Compound 3 (Cmp 3), and Compound 1 (Cmp 1), relative to FTY720-P. The data shown are the mean and standard error of the mean for EC50 values (nM) with n=4 independent experiments for AKT phosphorylation, and n=3 independent experiments for ERK phosphorylation following a 10-minute exposure to test compound.

FIG. 10 shows $EC_{50}$ values for AKT and ERK phosphorylation in primary mouse and human astrocytes with ozanimod, Compound 3, and Compound 1, relative to FTY720-P. The data shown are the mean and standard error of the mean for EC50 values (nM) with n=3 independent experiments for AKT phosphorylation, and n=3-5 independent experiments for ERK phosphorylation following a 10-minute exposure to test compound. ND=not determined.

DETAILED DESCRIPTION OF THE INVENTION

Figure 1:
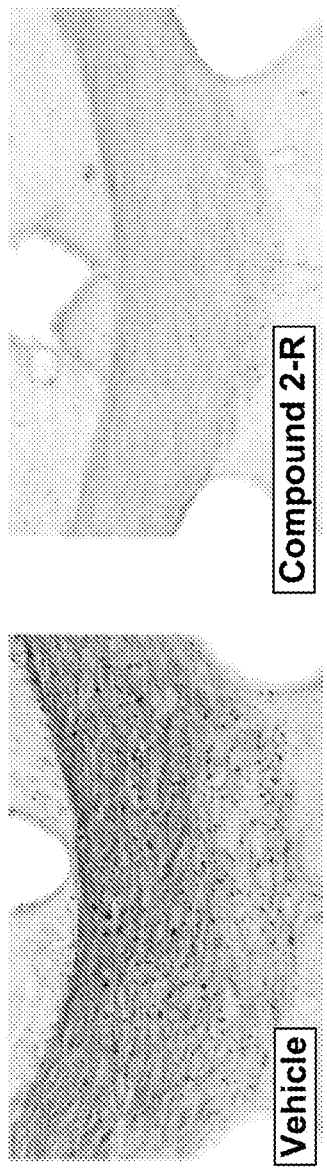
FIG. 1 shows the effect of Compound (2-R) on the number of swollen and transected axons in the cuprizone mouse model of demyelination. Histological analysis of mice treated with Compound (2-R) (1 mg/kg) (top right image) showed reduced neuronal breaks and fewer neuronal ovoids vs. vehicle treated mice (top left image) (32 v. 121 SMI-32-positive ovoids per 250,000 $\mu m^2$; $p<0.001$), suggesting that Comopund (2-R) preserved neuronal axons in the cuprizone-induced mouse model. Statistical comparisons were based on one-way analysis or variance.
Figure 1:
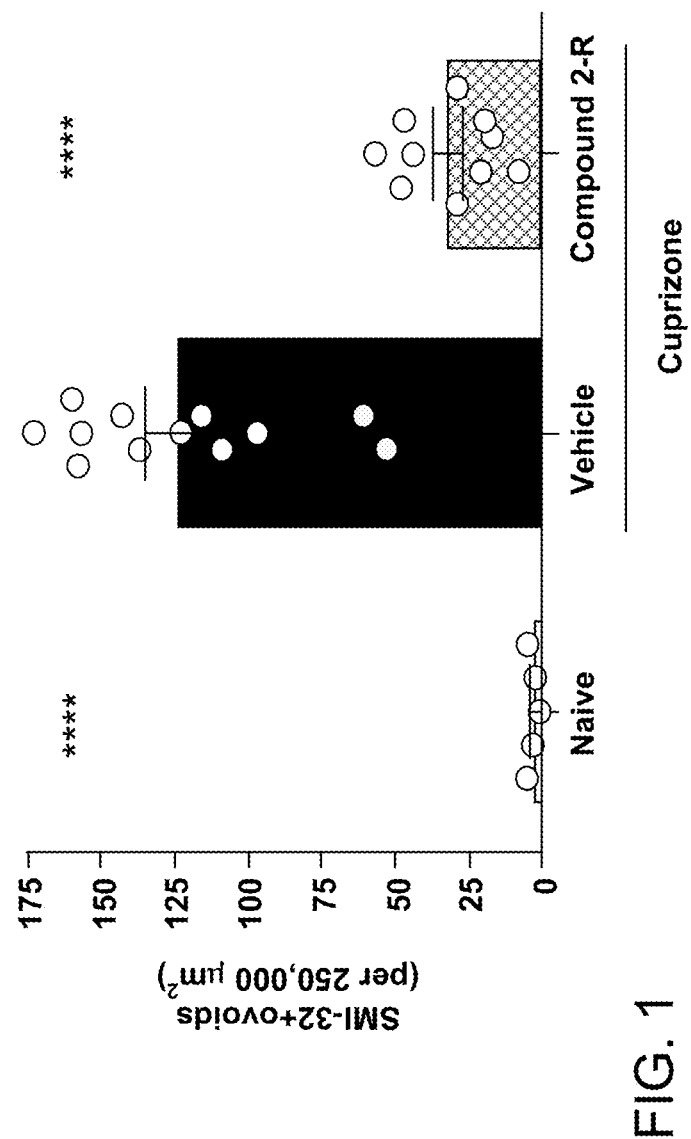

As used in the specification and the appended claims, the singular forms "a," "an" and "the" include plural referents unless the context clearly dictates otherwise.

The terms "comprising," "including," "having," "composed of," are open-ended terms as used herein, and do not preclude the existence of additional elements or components. In a claim element, use of the forms "comprising," "including," "having," or "composed of" means that whatever element is comprised, had, included, or composes is not necessarily the only element encompassed by the subject of the clause that contains that word.

As mentioned above, the present invention is generally directed to the use of S1P agonists in the context of S1P receptor-mediated neuroprotection, and in a more specific embodiment the S1P receptor agonist is ozanimod or a pharmaceutically acceptable salt, [ozanimod is a steriroisomer], homolog, hydrate or solvate thereof. Ozanomid is currently in clinical development for the treatment of relapsing multiple sclerosis (RMS) and ulcerative colitis (UC). Ozanimod has been found to selectively target the $S1P_1$ receptor and $S1P_5$ receptor, and has shown therapeutic benefit in clinical trials of relapsing multiple sclerosis (RRMS). Ozanimod down-modulates the $S1P_1$ receptor, resulting in retention of autoreactive lymphocytes in secondary lymphoid organs. Ozanimod is the hydrochloride salt of the following structure.

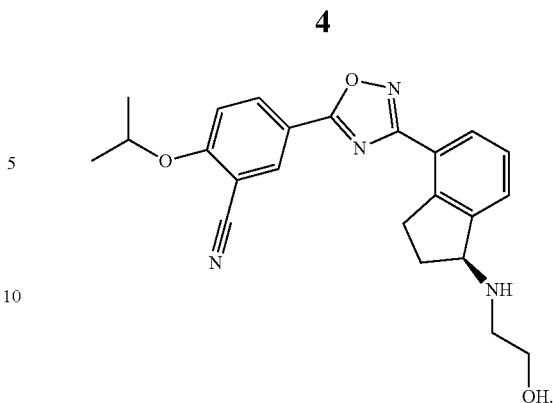

As depicted above, ozanimod is the S-isomeric form of the compound (i.e., as denoted by the solid "wedge" bond between the indane carbon atom and the nitrogen atom of the —NH $CH_2CH_2OH$ group). However, in the context of this disclosure, the R-isomer (as denoted by the dashed "wedge" bond) is also within the scope of this application, as shown below:

Accordingly, reference to the compound with "solid" lines, as depicted below, which is understood to include both the S and R isomeric forms:

In this regard, it should be understood that all chiral, diastereomeric, racemic forms of a structure are intended, unless a particular stereochemistry or isomeric form is specifically indicated. Compounds used in the present invention can include enriched or resolved optical isomers at any or all asymmetric atoms as are apparent from the depictions, at any degree of enrichment. Both racemic and diastereomeric mixtures, as well as the individual optical isomers can be synthesized so as to be substantially free of their enantiomeric or diastereomeric partners, and these are all within the scope of certain embodiments of the invention.

"Substantially" as the term is used herein means completely or almost completely; for example, a composition that is "substantially free" of a component either has none of the component or contains such a trace amount that any relevant functional property of the composition is unaffected by the presence of the trace amount, or a compound is "substantially pure" is there are only negligible traces of impurities present. For example, substantially enantiomerically pure means a level of enantiomeric enrichment of one enantiomer with respect to the other enantiomer of at least 90%, 95%, 98%, 99%, 99.5% or 99.9%.

As used herein, a "pharmaceutically acceptable salt" is a salt formed from an ion that has been approved for human consumption and is generally non-toxic. In the case of ozanimod, the structure of which is shown above, the pharmaceutically acceptable salt is the hydrochloride (HCl) salt, which is the form currently in clinical development for the treatment of RMS and UC.

As used herein, a "subject" means both mammals and non-mammals. Mammals include, for example, humans; non-human primates, e.g., apes and monkeys; cattle; horses; sheep; and goats. Non-mammals include, for example, fish and birds. "Subject" and "patient" are used interchangeably herein.

In one embodiment, the S1P receptor agonist is ozanimod.

In other embodiments, the S1P receptor agonist is a compound having the following structure, or a pharmaceutically acceptable salt, a racemic mixture, an individual stereoisomer, homolog, hydrate or solvate thereof:

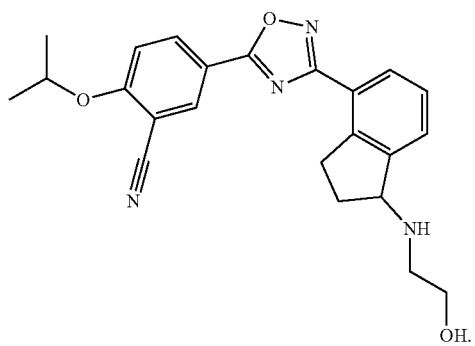 [SMILES: CC(C)Oc1ccc(-c2nc(-c3cccc4c3CCC4NCCO)no2)cc1C#N]

In a further embodiment, the S1P receptor agonist is a compound having one of the following structures, or a pharmaceutically acceptable salt, a racemic mixture, an individual stereoisomer, homolog, hydrate or solvate thereof:

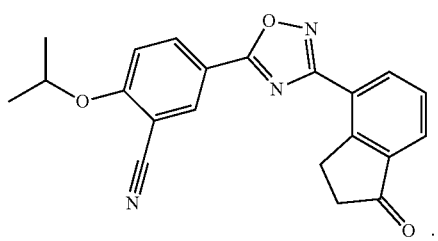

(1)

In a further embodiment, the S1P receptor agonist is a compound having one of the following structures, or a pharmaceutically acceptable salt, a racemic mixture, an individual stereoisomer, homolog, hydrate or solvate thereof:

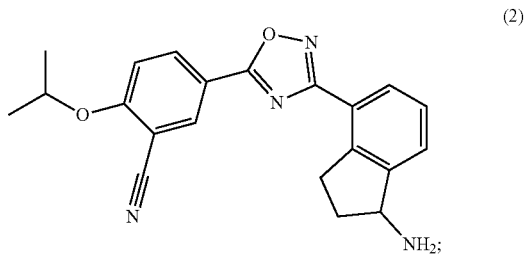

(2)

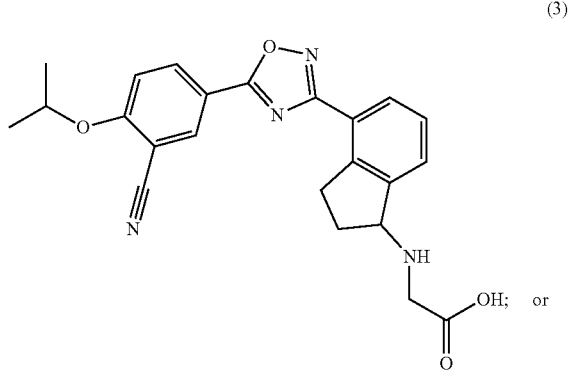

(3)

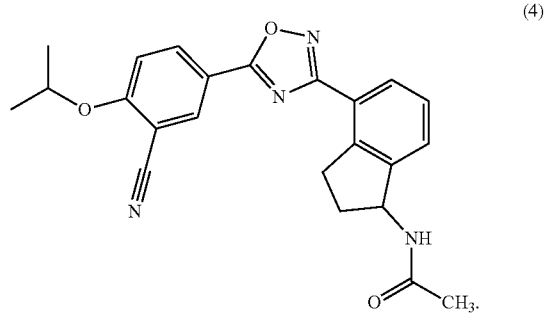

(4)

In a more specific embodiment, the S1P receptor agonist is a compound having one of the following structure, or a pharmaceutically acceptable salt, homolog, hydrate or solvate thereof:

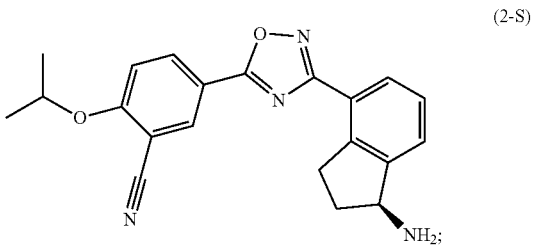

(2-S)

(3-S)

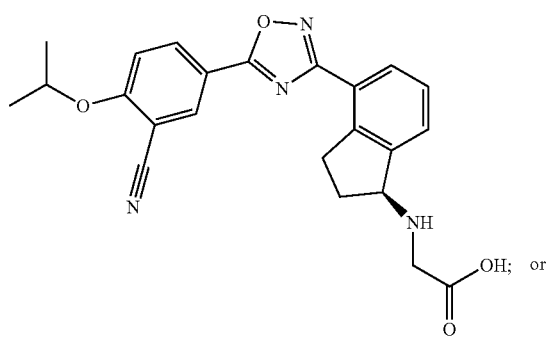

OH; or (4-R)

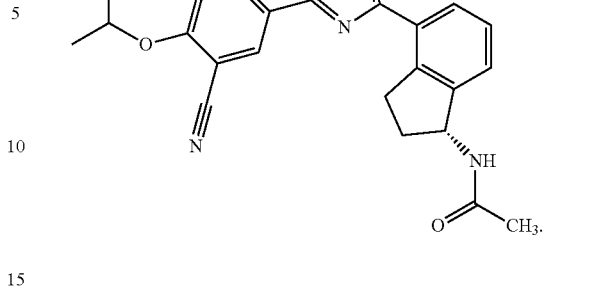

In another embodiment, the S1P receptor agonist is a compound having the following Structure (I):

(4-S)

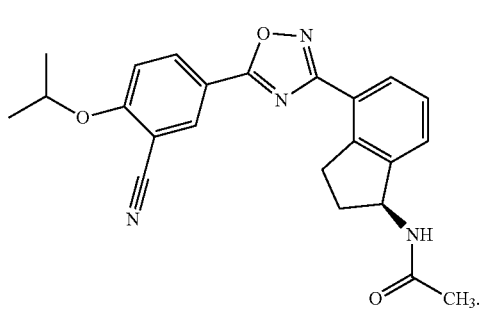

In a more specific embodiment, the S1P receptor agonist is a compound having one of the following structures, or a pharmaceutically acceptable salt, homolog, hydrate or solvate thereof:

(2-R)

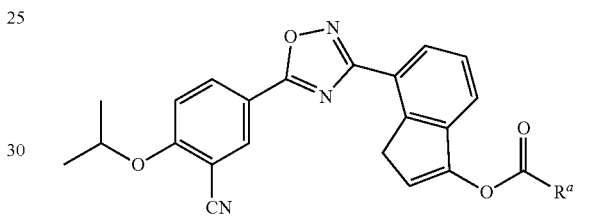

(I)

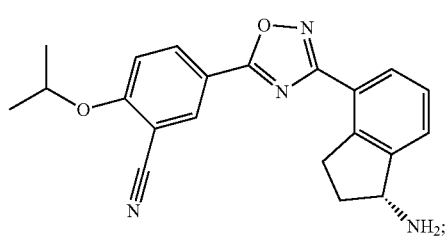

or a pharmaceutically acceptable salt, homolog, hydrate or solvate thereof, wherein:

$R^a$ is:

alkanediyl-$OR^{a1}$, alkanediyl-C(=O)$OR^{a2}$, alkyl or substituted alkyl, aryl, alkaryl, substituted aryl or substituted alkaryl;

heterocyclyl, substituted heterocyclyl, heterocyclyalkyl or substituted heterocyclylalkyl; and $R^{a1}$ and $R^{a2}$ are independently H or $C_{1-4}$alkyl.

In another embodiment, the S1P agonist is a compound of Structure (I) above, or a pharmaceutically acceptable salt, isomer, racemate, homolog, hydrate or solvate thereof, wherein:

$R^a$ is:

alkanediyl-$OR^{a1}$, alkanediyl-C(=O)$OR^{a2}$, substituted alkyl, aryl or substituted aryl, or heterocyclyl, substituted heterocyclyl, heterocyclyalkyl or substituted heterocyclylalkyl; and $R^{a1}$ and $R^{a2}$ are independently H or $C_{1-4}$alkyl.

In another embodiment, the S1P agonist is a compound of Structure (I) above, or a pharmaceutically acceptable salt, homolog, hydrate or solvate thereof, wherein $R^a$ is not $C_{1-4}$ alkyl, and in a further embodiment is not methyl or tert-butyl.

(3-R)

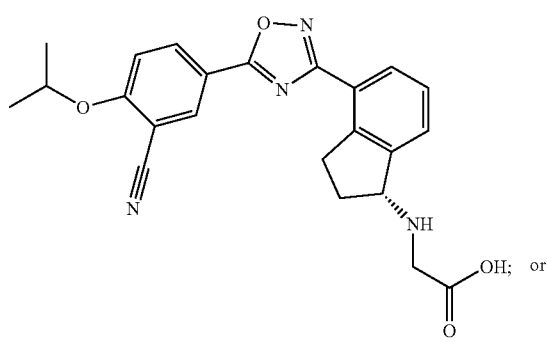

OH; or

Representative compounds of Formula (I) are listed in Table 1.

TABLE 1

| Cpd No. | Structure |
| --- | --- |
| I-1 | 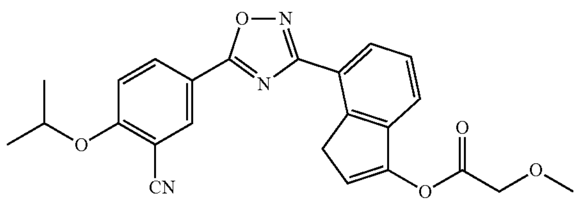 [SMILES: COCC(=O)OC1=CCc2c1cccc2-c1noc(-c2ccc(OC(C)C)c(C#N)c2)n1] |
| I-2 | 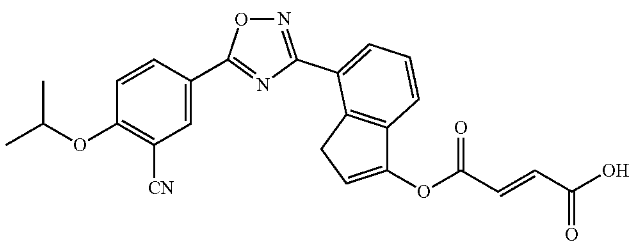 [SMILES: CC(C)Oc1ccc(-c2nc(-c3cccc4c3CC=C4OC(=O)/C=C/C(=O)O)no2)cc1C#N] |
| I-3 | 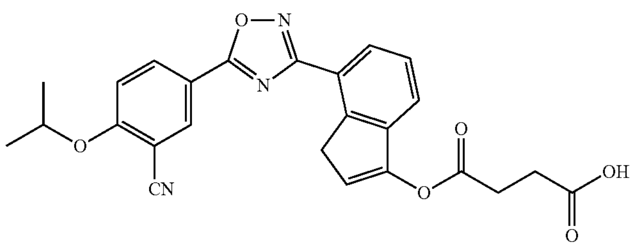 [SMILES: CC(C)Oc1ccc(-c2nc(-c3cccc4c3CC=C4OC(=O)CCC(=O)O)no2)cc1C#N] |
| I-4 | 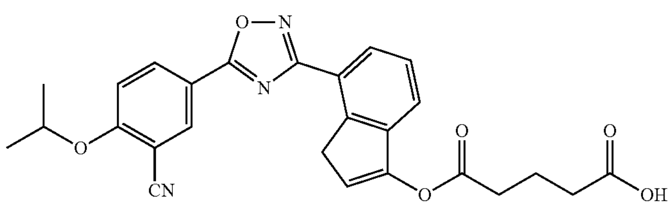 [SMILES: CC(C)Oc1ccc(-c2nc(-c3cccc4c3CC=C4OC(=O)CCCC(=O)O)no2)cc1C#N] |
| I-5 | 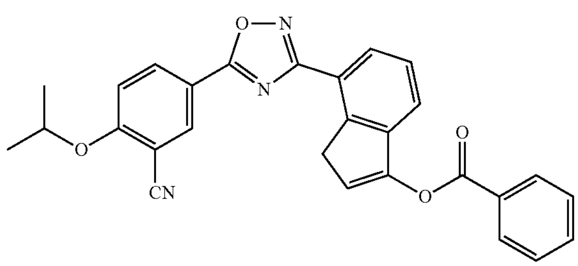 [SMILES: CC(C)Oc1ccc(-c2nc(-c3cccc4c3CC=C4OC(=O)c3ccccc3)no2)cc1C#N] |
| I-6 | 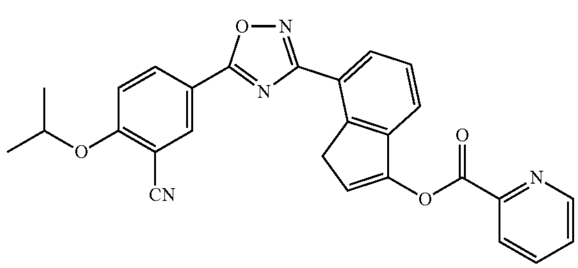 [SMILES: CC(C)Oc1ccc(-c2nc(-c3cccc4c3CC=C4OC(=O)c3ccccn3)no2)cc1C#N] |

TABLE 1-continued

| Cpd No. | Structure |
|---|---|
| I-7 | 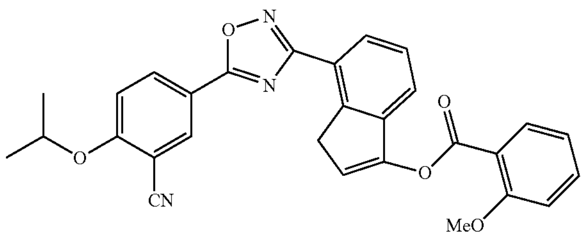 [SMILES: COc1ccccc1C(=O)OC1=CCc2c1cccc2-c1noc(-c2ccc(OC(C)C)c(C#N)c2)n1] |
| I-8 | 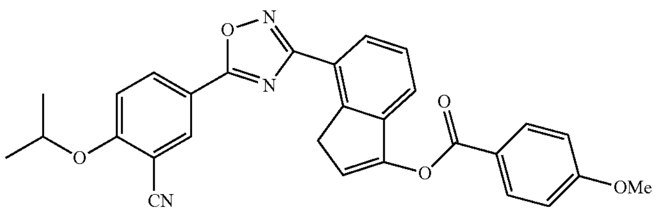 [SMILES: COc1ccc(C(=O)OC2=CCc3c2cccc3-c2noc(-c3ccc(OC(C)C)c(C#N)c3)n2)cc1] |
| I-9 | 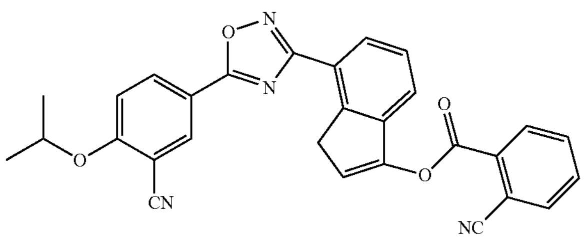 [SMILES: CC(C)Oc1ccc(-c2nc(-c3cccc4c3CC=C4OC(=O)c3ccccc3C#N)no2)cc1C#N] |
| I-10 | 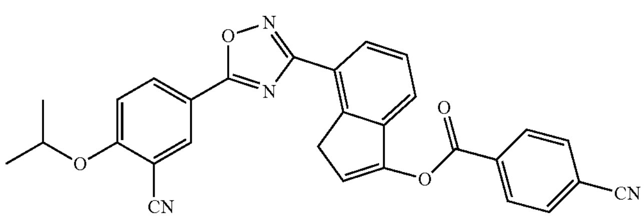 [SMILES: CC(C)Oc1ccc(-c2nc(-c3cccc4c3CC=C4OC(=O)c3ccc(C#N)cc3)no2)cc1C#N] |
| I-11 | 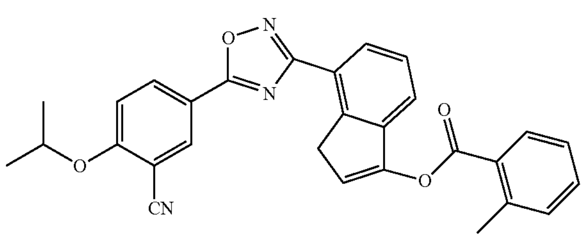 [SMILES: Cc1ccccc1C(=O)OC1=CCc2c1cccc2-c1noc(-c2ccc(OC(C)C)c(C#N)c2)n1] |
| I-12 | 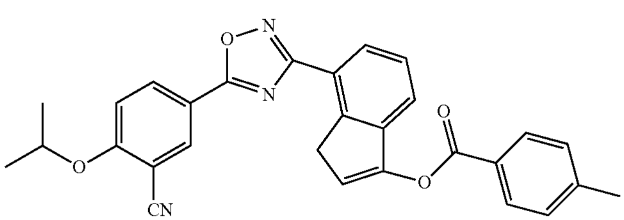 [SMILES: Cc1ccc(C(=O)OC2=CCc3c2cccc3-c2noc(-c3ccc(OC(C)C)c(C#N)c3)n2)cc1] |
| I-13 | 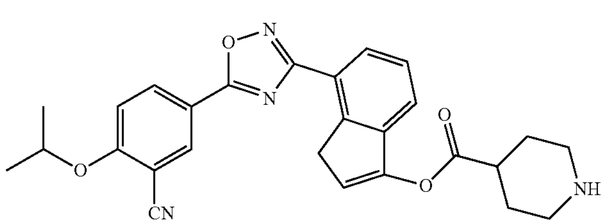 [SMILES: CC(C)Oc1ccc(-c2nc(-c3cccc4c3CC=C4OC(=O)C3CCNCC3)no2)cc1C#N] |

TABLE 1-continued
| Cpd No. | Structure |
|---|---|
| I-14 | 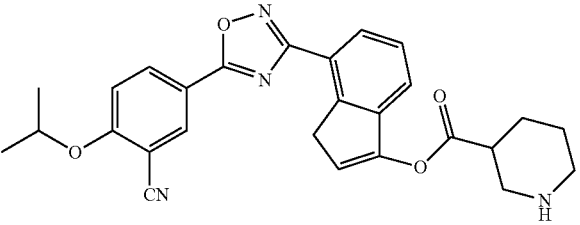 [SMILES: CC(C)Oc1ccc(-c2nc(-c3cccc4c3CC=C4OC(=O)C3CCCNC3)no2)cc1C#N] |
| I-15 | 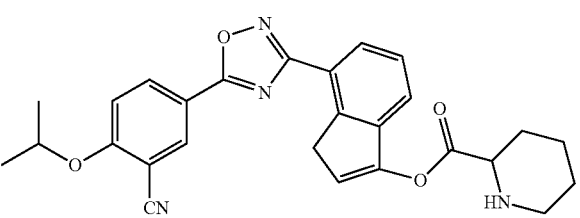 [SMILES: CC(C)Oc1ccc(-c2nc(-c3cccc4c3CC=C4OC(=O)C3CCCCN3)no2)cc1C#N] |
| I-16 | 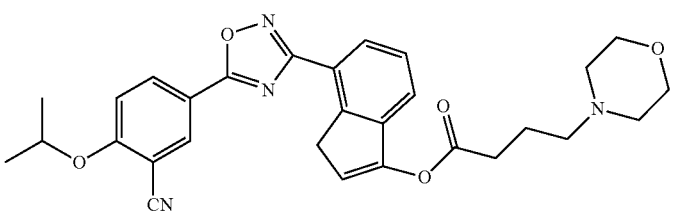 [SMILES: CC(C)Oc1ccc(-c2nc(-c3cccc4c3CC=C4OC(=O)CCCN3CCOCC3)no2)cc1C#N] |
| I-17 | 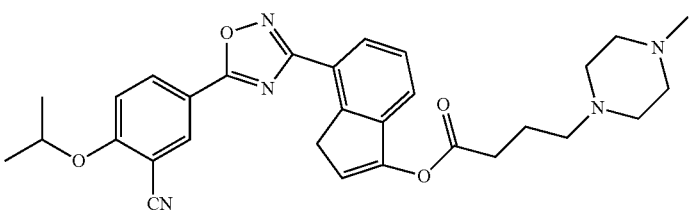 [SMILES: CC(C)Oc1ccc(-c2nc(-c3cccc4c3CC=C4OC(=O)CCCN3CCN(C)CC3)no2)cc1C#N] |
| I-18 | 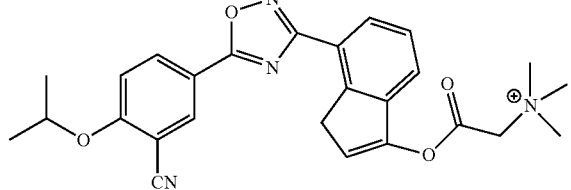 |
| I-19 | 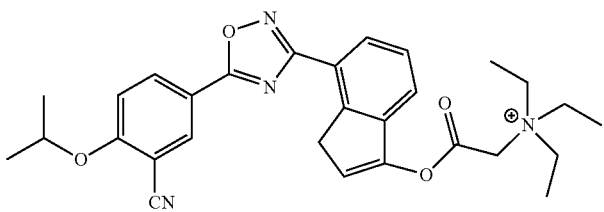 [SMILES: CC[N+](CC)(CC)CC(=O)OC1=CCc2c1cccc2-c1noc(-c2ccc(OC(C)C)c(C#N)c2)n1] |
| I-20 | 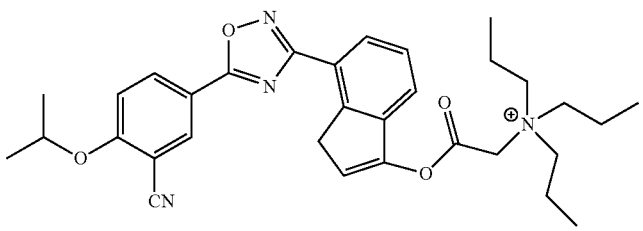 [SMILES: CCC[N+](CCC)(CCC)CC(=O)OC1=CCc2c1cccc2-c1noc(-c2ccc(OC(C)C)c(C#N)c2)n1] |

TABLE 1-continued

| Cpd No. | Structure |
|---|---|
| I-21 | 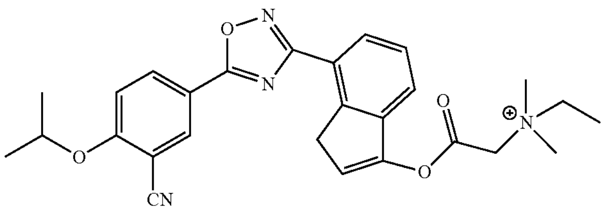 [SMILES: CC[N+](C)(C)CC(=O)OC1=CCc2c1cccc2-c1noc(-c2ccc(OC(C)C)c(C#N)c2)n1] |
| I-22 | 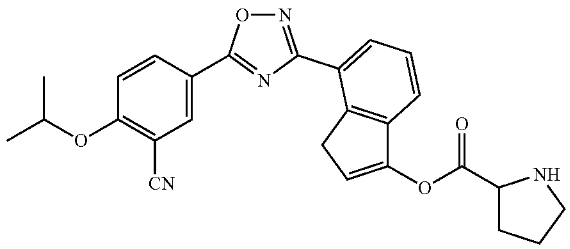 [SMILES: CC(C)Oc1ccc(-c2nc(-c3cccc4c3CC=C4OC(=O)C3CCCN3)no2)cc1C#N] |
| I-23 | 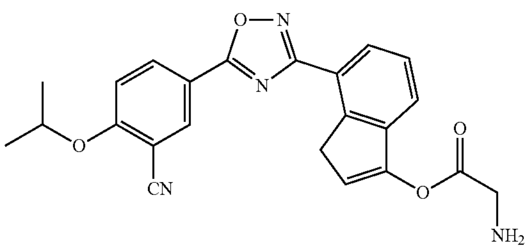 [SMILES: CC(C)Oc1ccc(-c2nc(-c3cccc4c3CC=C4OC(=O)CN)no2)cc1C#N] |
| I-24 | 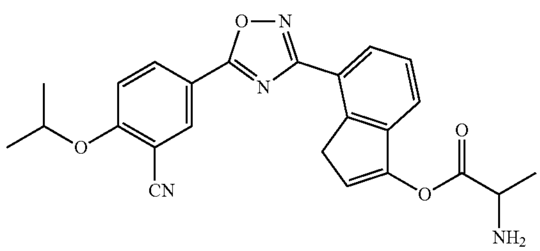 [SMILES: CC(C)Oc1ccc(-c2nc(-c3cccc4c3CC=C4OC(=O)C(C)N)no2)cc1C#N] |
| I-25 | 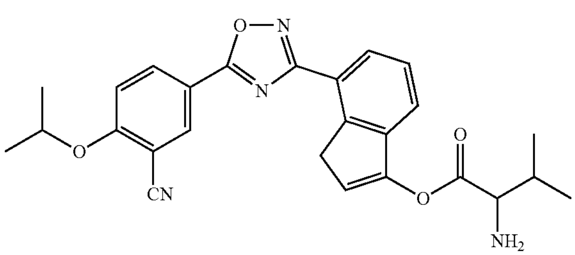 [SMILES: CC(C)Oc1ccc(-c2nc(-c3cccc4c3CC=C4OC(=O)C(N)C(C)C)no2)cc1C#N] |
| I-26 | 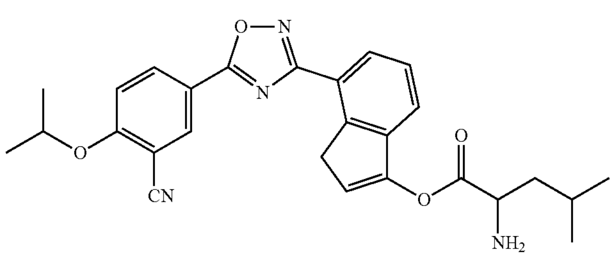 [SMILES: CC(C)CC(N)C(=O)OC1=CCc2c1cccc2-c1noc(-c2ccc(OC(C)C)c(C#N)c2)n1] |

TABLE 1-continued

| Cpd No. | Structure |
|---|---|
| I-27 | (structure) |
| I-28 | (structure) |
| I-29 | (structure) |
| I-30 | (structure) |
| I-31 | (structure) |
| I-32 | (structure) |

TABLE 1-continued

| Cpd No. | Structure |
|---|---|
| I-33 | 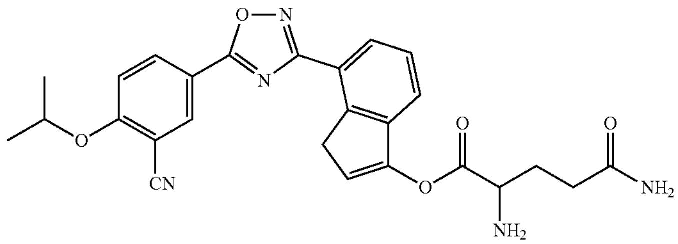 [SMILES: CC(C)Oc1ccc(-c2nc(-c3cccc4c3CC=C4OC(=O)C(N)CCC(N)=O)no2)cc1C#N] |
| I-34 | 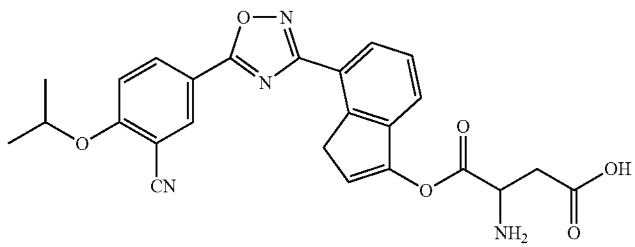 [SMILES: CC(C)Oc1ccc(-c2nc(-c3cccc4c3CC=C4OC(=O)C(N)CC(=O)O)no2)cc1C#N] |
| I-35 | 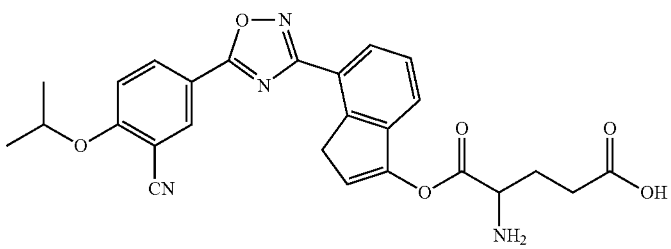 [SMILES: CC(C)Oc1ccc(-c2nc(-c3cccc4c3CC=C4OC(=O)C(N)CCC(=O)O)no2)cc1C#N] |
| I-36 | 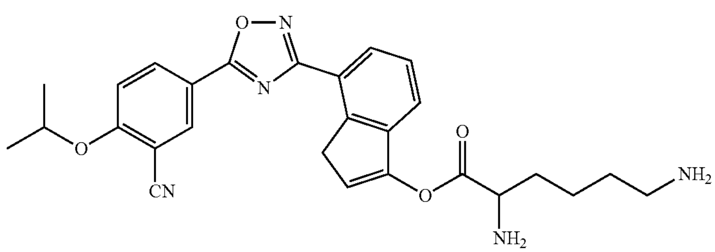 [SMILES: CC(C)Oc1ccc(-c2nc(-c3cccc4c3CC=C4OC(=O)C(N)CCCCN)no2)cc1C#N] |
| I-37 | 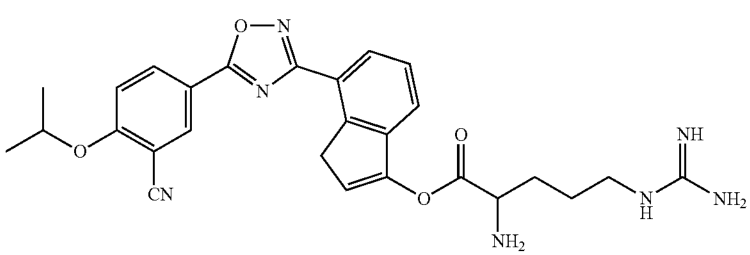 [SMILES: CC(C)Oc1ccc(-c2nc(-c3cccc4c3CC=C4OC(=O)C(N)CCCNC(=N)N)no2)cc1C#N] |
| I-38 | 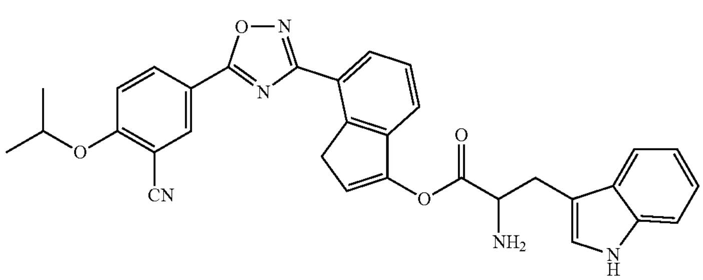 [SMILES: CC(C)Oc1ccc(-c2nc(-c3cccc4c3CC=C4OC(=O)C(N)Cc3c[nH]c4ccccc34)no2)cc1C#N] |

TABLE 1-continued

| Cpd No. | Structure |
|---|---|
| I-39 | 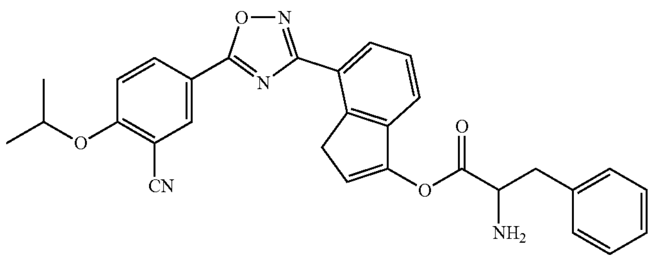 [SMILES: CC(C)Oc1ccc(-c2nc(-c3cccc4c3CC=C4OC(=O)C(N)Cc3ccccc3)no2)cc1C#N] |
| I-40 | 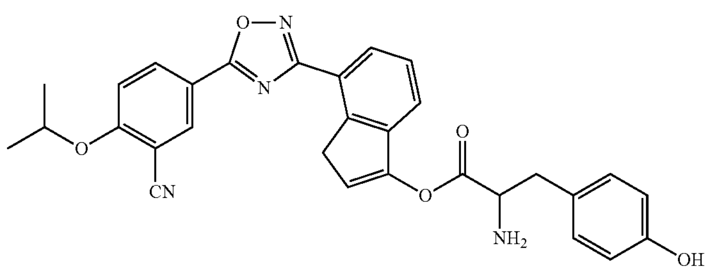 [SMILES: CC(C)Oc1ccc(-c2nc(-c3cccc4c3CC=C4OC(=O)C(N)Cc3ccc(O)cc3)no2)cc1C#N] |
| I-41 | 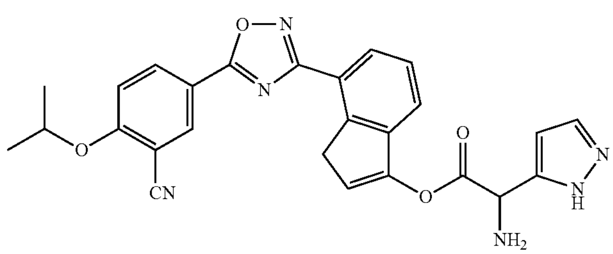 [SMILES: CC(C)Oc1ccc(-c2nc(-c3cccc4c3CC=C4OC(=O)C(N)c3ccn[nH]3)no2)cc1C#N] |

In another embodiment, the S1P receptor agonist is a compound of Structure (II):

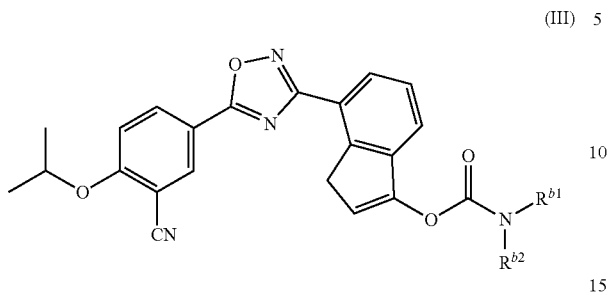

(III)

or a pharmaceutically acceptable salt, homolog, hydrate or solvate thereof, wherein $R^{b1}$ and $R^{b2}$ are independently:
- hydrogen, alky or substituted alkyl;
- or $R^{b1}$ and $R^{b2}$ are taken together with the nitrogen to which they are attached form heterocyclyl or substituted heterocylyl.

Representative compounds of Structure (II) are listed in Table 2.

TABLE 2

| Cpd No. | Structure |
|---|---|
| II-1 | 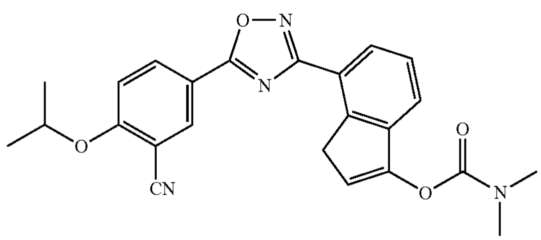 [SMILES: CC(C)Oc1ccc(-c2nc(-c3cccc4c3CC=C4OC(=O)N(C)C)no2)cc1C#N] |
| II-2 | 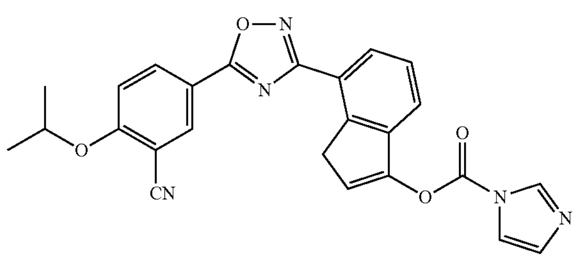 [SMILES: CC(C)Oc1ccc(-c2nc(-c3cccc4c3CC=C4OC(=O)n3ccnc3)no2)cc1C#N] |
| II-3 | 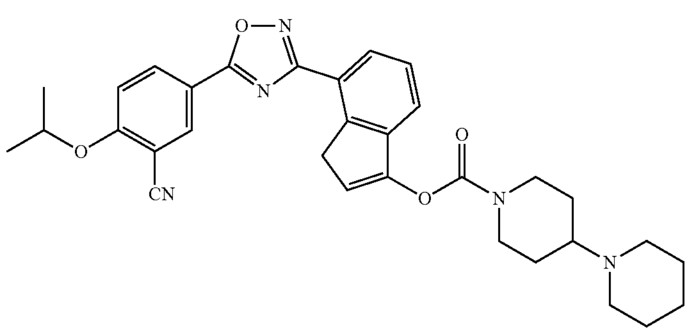 [SMILES: CC(C)Oc1ccc(-c2nc(-c3cccc4c3CC=C4OC(=O)N3CCC(N4CCCCC4)CC3)no2)cc1C#N] |

TABLE 2-continued

| Cpd No. | Structure |
|---|---|
| II-4 | 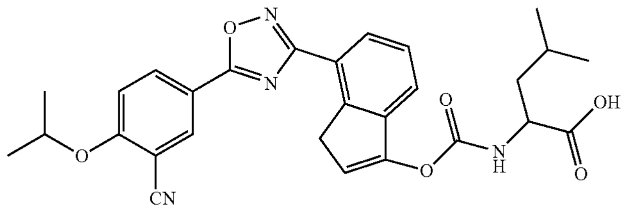 [SMILES: CC(C)CC(NC(=O)OC1=CCc2c1cccc2-c1noc(-c2ccc(OC(C)C)c(C#N)c2)n1)C(=O)O] |
| II-5 | 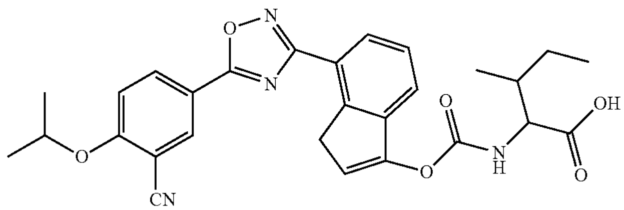 [SMILES: CCC(C)C(NC(=O)OC1=CCc2c1cccc2-c1noc(-c2ccc(OC(C)C)c(C#N)c2)n1)C(=O)O] |
| II-6 | 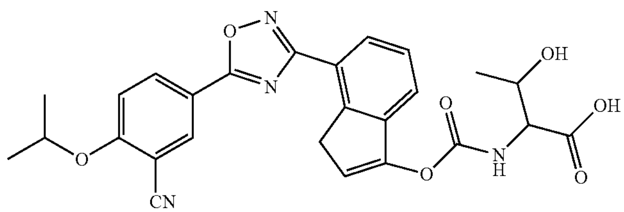 [SMILES: CC(C)Oc1ccc(-c2nc(-c3cccc4c3CC=C4OC(=O)NC(C(=O)O)C(C)O)no2)cc1C#N] |
| II-7 | 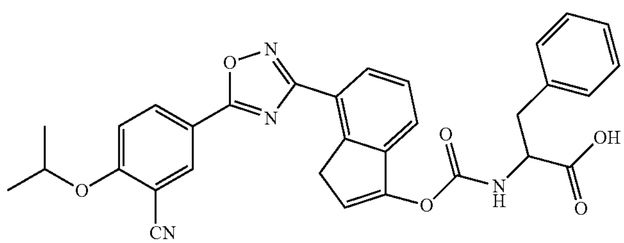 [SMILES: CC(C)Oc1ccc(-c2nc(-c3cccc4c3CC=C4OC(=O)NC(Cc3ccccc3)C(=O)O)no2)cc1C#N] |

In yet another embodiment, the S1P receptor agonist is a compound of Structure (III):

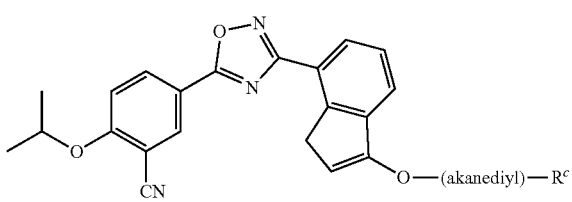

(III)

or a pharmaceutically acceptable salt, homolog, hydrate or solvate thereof, wherein $R^1$ is:

—$OR^{a1}$ or —$NR^{c2}R^{c3}$;

$R^{c1}$ is hydrogen, alky, substituted alkyl, —C(=O)(alkyl), —C(=O)(substituted alkyl), —C(=O)O(alkyl) or —C(=O)O(substituted alkyl); and $R^{c2}$ and $R^{c3}$ are independently hydrogen, alky or substituted alkyl;

or $R^{c2}$ and $R^{c3}$ are taken together with the nitrogen to which they are attached form heterocyclyl or substituted heterocyclyl.

Representative compounds of Structure (III) are listed in Table 3.

TABLE 3

| Cpd No. | Structure |
|---|---|
| III-1 | 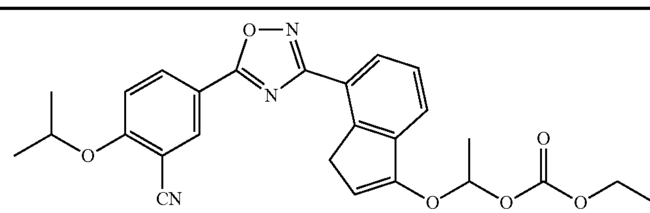 |

TABLE 3-continued

| Cpd No. | Structure |
|---|---|
| III-2 | 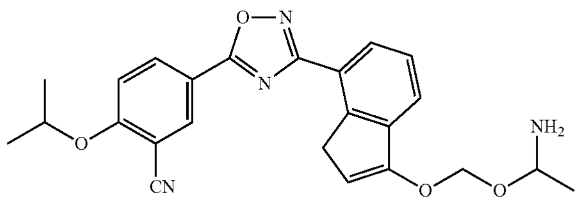 [SMILES: CC(C)Oc1ccc(-c2nc(-c3cccc4c3CC=C4OCOC(C)N)no2)cc1C#N] |
| III-3 | 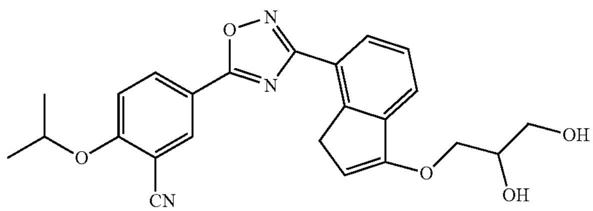 [SMILES: CC(C)Oc1ccc(-c2nc(-c3cccc4c3CC=C4OCC(O)CO)no2)cc1C#N] |
| III-4 | 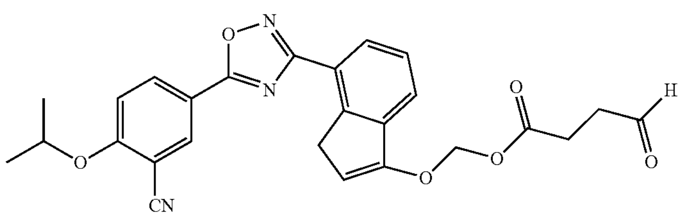 [SMILES: CC(C)Oc1ccc(-c2nc(-c3cccc4c3CC=C4OCOC(=O)CCC=O)no2)cc1C#N] |
| III-5 | 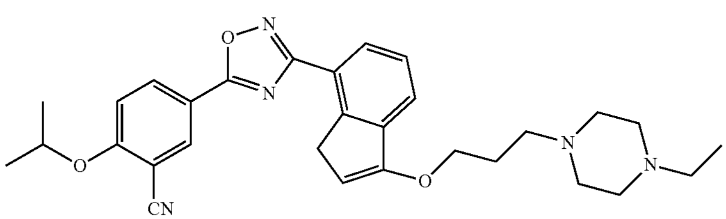 [SMILES: CCN1CCN(CCCOC2=CCc3c2cccc3-c2noc(-c3ccc(OC(C)C)c(C#N)c3)n2)CC1] |
| III-6 | 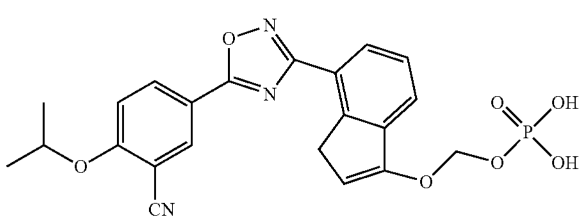 [SMILES: CC(C)Oc1ccc(-c2nc(-c3cccc4c3CC=C4OCOP(=O)(O)O)no2)cc1C#N] |
| III-7 | 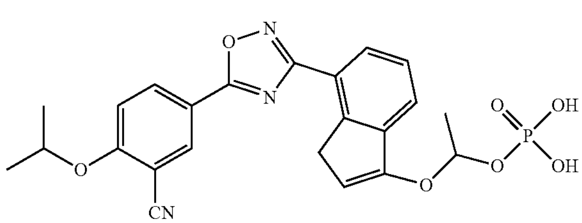 [SMILES: CC(C)Oc1ccc(-c2nc(-c3cccc4c3CC=C4OC(C)OP(=O)(O)O)no2)cc1C#N] |

In different embodiments, the S1P receptor agonist is a compound of Structure (IV):

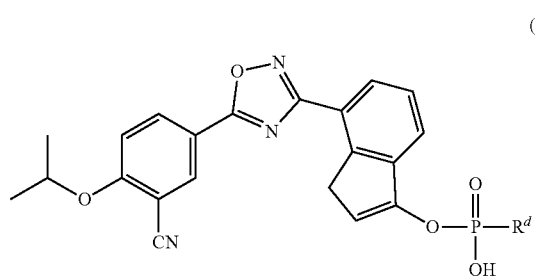

(IV)

or a pharmaceutically acceptable salt, homolog, hydrate or solvate thereof, wherein $R^d$ is:

—$OR^{d1}$, or

—$N(R^{d2})(R^{d3})$; and $R^{d1}$, $R^{d2}$, and $R^{d3}$ are independently H or $C_{1-4}$alkyl, or $R^{d2}$ and $R^{d3}$ are taken together with the nitrogen to which they are attached form a heterocyclyl or substituted heterocyclyl.

Representative compounds of Formula (IV) are listed in Table 4.

TABLE 4

| Cpd No. | Structure |
|---|---|
| IV-1 | 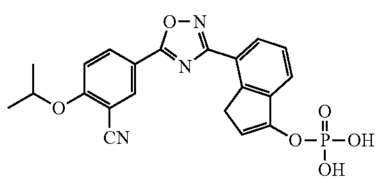 [SMILES: CC(C)Oc1ccc(-c2nc(-c3cccc4c3CC=C4OP(=O)(O)O)no2)cc1C#N] |
| IV-2 | 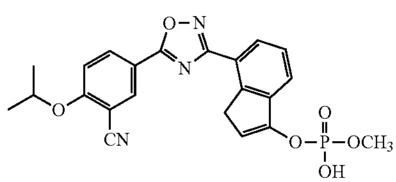 [SMILES: COP(=O)(O)OC1=CCc2c1cccc2-c1noc(-c2ccc(OC(C)C)c(C#N)c2)n1] |
| IV-3 | 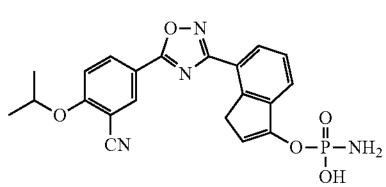 [SMILES: CC(C)Oc1ccc(-c2nc(-c3cccc4c3CC=C4OP(N)(=O)O)no2)cc1C#N] |

In more embodiments, the S1P receptor agonist is a compound of Structure (V):

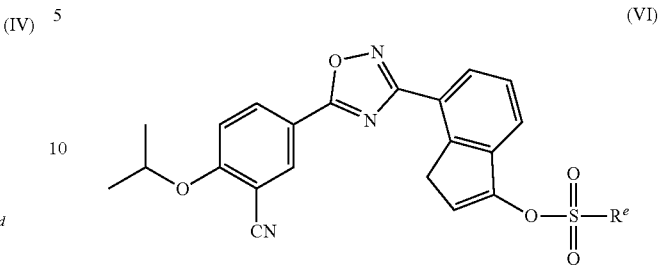

(VI)

or a pharmaceutically acceptable salt, homolog, hydrate or solvate thereof, wherein $R^e$ is:

—$OR^{e1}$, or

—$N(R^{e2})(R^{e3})$, and $R^{e1}$, $R^{e2}$ and $R^{e3}$ are independently H or $C_{1-4}$alkyl, or $R^{e2}$ and $R^{e3}$ are taken together with the nitrogen to which they are attached form a heterocyclyl or substituted heterocyclyl.

Representative compounds of Formula (V) are listed in Table 5.

TABLE 5

| Cpd No. | Structure |
|---|---|
| V-1 | 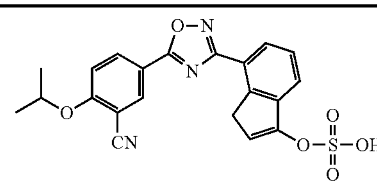 |
| V-3 | 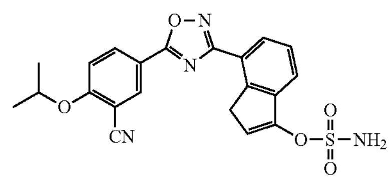 [SMILES: CC(C)Oc1ccc(-c2nc(-c3cccc4c3CC=C4OS(N)(=O)=O)no2)cc1C#N] |

As used in Structures (I-V), the following terms have the meanings set forth below.

"Alkanediyl" means a divalent radical such as methylene (—$CH_2$—) derived from an alkyl group by removal of two hydrogen atoms. Accordingly, any alkyl group as defined herein constitutes an alkanediyl by removal of two hydrogen atoms to render a divalent radical.

"Alkyl" means straight chain, branched or cyclic alkyl group (cycloalkyl), saturated or unsaturated, having from 1 to about 20 carbon atoms ($C_{1-20}$ alkyl), and from 3 to 20 carbon atoms in the case of cycloalkyl. Alkyls are typically from 1 to 12 carbons ($C_{1-12}$ alkyl) or, in some embodiments, from 1 to 8 carbon atoms ($C_{1-8}$ alkyl) or, in some embodiments, from 1 to 4 carbon atoms ($C_{1-4}$ alkyl) or, in some embodiments, from 1 to 3 carbon atoms ($C_{1-3}$ alkyl). Examples of straight chain alkyl groups include, but are not limited to methyl, ethyl, n-propyl, n-butyl, n-pentyl, n-hexyl, n-heptyl, and n-octyl groups. Examples of branched alkyl groups include, but are not limited to, isopropyl, iso-butyl, sec-butyl, t-butyl, neopentyl, isopentyl, and 2,2-dimethylpropyl groups. Examples of unsaturated alkyls include alkenyl and alkynyl groups. Examples of cycloalkyl include, but are not limited to, cyclopropyl, cyclobutyl, cyclopentyl, cyclohexyl, cycloheptyl, and cyclooctyl groups. In some embodiments, the cycloalkyl group has 3 to 8 ring members, whereas in other embodiments the number of ring carbon atoms range from 3 to 5, 3 to 6, or 3 to 7. Cycloalkyl groups further include polycyclic cycloalkyl groups such as, but not limited to, norbornyl, adamantyl, bornyl, camphenyl, isocamphenyl, and carenyl groups, and fused rings such as, but not limited to, decalinyl, and the like.

"Alkenyl" means a straight chain, branched or cyclic alkyl group as defined above, wherein at least one double bond exists between two carbon atoms. Thus, alkenyl groups have from 2 to about 20 carbon atoms, and typically from 2 to 12 carbons or, in some embodiments, from 2 to 8 carbon atoms. Examples include, but are not limited to CH=CH(CH$_3$), CH=C(CH$_3$)$_2$, C(CH$_3$)=CH$_2$, C(CH$_3$)=CH(CH$_3$), C(CH$_2$CH$_3$)=CH$_2$, vinyl, cyclohexenyl, cyclopentenyl, cyclohexadienyl, butadienyl, pentadienyl, and hexadienyl among others.

"Alkynyl" means a straight chain, branched or cyclic alkyl group as defined above, wherein at least one triple bond exists between two carbon atoms. Thus, alkynyl groups have from 2 to about 20 carbon atoms, and typically from 2 to 12 carbons or, in some embodiments, from 2 to 8 carbon atoms. Examples include, but are not limited to —C≡CH, —C≡C(CH$_3$), —C≡C(CH$_2$CH$_3$), CH$_2$C≡CH, CH$_2$C≡C(CH$_3$), and CH$_2$C≡C(CH$_2$CH$_3$), among others.

"Aryl" means a cyclic aromatic hydrocarbon that does not contain a heteroatom (a "heteroatom" refers to non-carbon and non-hydrogen atoms, capable of forming covalent bonds with carbon, and are typically N, O, S and P). Aryl includes, but is not limited to, phenyl, azulenyl, heptalenyl, biphenyl, indacenyl, fluorenyl, phenanthrenyl, triphenylenyl, pyrenyl, naphthacenyl, chrysenyl, biphenylenyl, anthracenyl, and naphthyl groups. In some embodiments, aryl groups contain 6-14 carbons in the ring portions of the groups. Aryl also includes fused rings, such as fused aromatic-aliphatic ring systems (e.g., indanyl, tetrahydronaphthyl, and the like).

"Arylalkyl" means an alkyl group as defined above in which a hydrogen or carbon bond of the alkyl group is replaced with a bond to an aryl group as defined above. Arylalkyl includes, for example, benzyl (i.e., —CH$_2$-phenyl).

"Heterocyclyl" means aromatic (heteroaryl) and non-aromatic ring compounds containing 3 or more ring members, of which one or more is a heteroatom. In some embodiments, heterocyclyl includes 3 to 20 ring members, whereas other such groups have 3 to 15 ring members. At least one ring contains a heteroatom, but every ring in a polycyclic system need not contain a heteroatom. For example, a dioxolanyl ring and a benzdioxolanyl ring system (methylenedioxyphenyl ring system) are both heterocyclyl groups within the meaning herein. A heterocyclyl group designated as a C2-heterocyclyl can be a 5-membered ring with two carbon atoms and three heteroatoms, a 6-membered ring with two carbon atoms and four heteroatoms and so forth. Likewise a C4-heterocyclyl can be a 5-membered ring with one heteroatom, a 6-membered ring with two heteroatoms, and so forth. The number of carbon atoms plus the number of heteroatoms sums up to equal the total number of ring atoms. A saturated heterocyclic ring refers to a heterocyclic ring containing no unsaturated carbon atoms. Heterocyclic rings include fused ring species, including those having fused aromatic and non-aromatic groups. They also includes polycyclic ring systems containing a heteroatom such as, but not limited to, quinuclidyl.

Representative heterocyclyls include, but are not limited to, pyrrolidinyl, furanyl, tetrahydrofuranyl, dioxolanyl, piperidinyl, piperazinyl, morpholinyl, pyrrolyl, pyrazolyl, triazolyl, tetrazolyl, oxazolyl, isoxazolyl, thiazolyl, pyridinyl, thiophenyl, benzothiophenyl, benzofuranyl, dihydrobenzofuranyl, indolyl, dihydroindolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, quinoxalinyl, and quinazolinyl groups.

"Heterocyclylalkyl" means an alkyl group as defined above in which a hydrogen or carbon bond of the alkyl group is replaced with a bond to a heterocyclyl group as defined above.

"Heteroaryl" means an aromatic heterocyclyl containing 5 or more ring members, of which, one or more is a heteroatom. A heteroaryl group designated as a C2-heteroaryl can be a 5-membered ring with two carbon atoms and three heteroatoms, a 6-membered ring with two carbon atoms and four heteroatoms and so forth. Likewise a C4-heteroaryl can be a 5-membered ring with one heteroatom, a 6-membered ring with two heteroatoms, and so forth. The number of carbon atoms plus the number of heteroatoms sums up to equal the total number of ring atoms.

Representative heteroaryls include, but are not limited to, pyrrolyl, pyrazolyl, triazolyl, tetrazolyl, oxazolyl, isoxazolyl, thiazolyl, pyridinyl, thiophenyl, benzothiophenyl, benzofuranyl, indolyl, azaindolyl, indazolyl, benzimidazolyl, azabenzimidazolyl, benzoxazolyl, benzothiazolyl, benzothiadiazolyl, imidazopyridinyl, isoxazolopyridinyl, thianaphthalenyl, purinyl, xanthinyl, adeninyl, guaninyl, quinolinyl, isoquinolinyl, tetrahydroquinolinyl, tetrahydroisoquinolinyl, quinoxalinyl, and quinazolinyl groups. Heteroaryls also include fused ring compounds, such as when at least one ring, but not necessarily all rings, are aromatic, including tetrahydroquinolinyl, tetrahydroisoquinolinyl, indolyl and 2,3-dihydro indolyl.

"Heteroarylalkyl" means an alkyl group as defined above in which a hydrogen or carbon bond of the alkyl group is replaced with a bond to a heteroaryl group as defined above.

Additional examples of aryl and heteroaryl groups include but are not limited to phenyl, biphenyl, indenyl, naphthyl (1-naphthyl, 2-naphthyl), N-hydroxytetrazolyl, N-hydroxytriazolyl, N hydroxyimidazolyl, anthracenyl (1-anthracenyl, 2-anthracenyl, 3-anthracenyl), thiophenyl (2 thienyl, 3-thienyl), furyl (2-furyl, 3-furyl), indolyl, oxadiazolyl, isoxazolyl, quinazolinyl, fluorenyl, xanthenyl, isoindanyl, benzhydryl, acridinyl, thiazolyl, pyrrolyl (2-pyrrolyl), pyrazolyl (3-pyrazolyl), imidazolyl (1-imidazolyl, 2-imidazolyl, 4 imidazolyl, 5-imidazolyl), triazolyl (1,2,3-triazol-1-yl, 1,2, 3-triazol-2-yl 1,2,3-triazol-4-yl,1,2,4azol-3-yl), oxazolyl (2-oxazolyl, 4-oxazolyl, 5-oxazolyl), thiazolyl (2-thiazolyl, 4-thiazolyl, 5-thiazolyl), pyridyl (2-pyridyl, 3 pyridyl, 4-pyridyl), pyrimidinyl (2-pyrimidinyl, 4-pyrimidinyl, 5-pyrimidinyl, 6-pyrimidinyl), pyrazinyl, pyridazinyl (3-pyridazinyl, 4-pyridazinyl, 5-pyridazinyl), quinolyl (2-quinolyl, 3 quinolyl, 4-quinolyl, 5-quinolyl, 6-quinolyl, 7-quinolyl, 8-quinolyl), isoquinolyl (1-isoquinolyl, 3-isoquinolyl, 4-isoquinolyl, 5-isoquinolyl, 6-isoquinolyl, 7-isoquinolyl, 8-isoquinolyl), benzo[b]furanyl (2-benzo[b]furanyl, 3-benzo[b]furanyl, 4-benzo[b]furanyl, 5-benzo[b]furanyl, 6 benzo[b]furanyl, 7-benzo[b]furanyl), 2,3-dihydro-benzo[b] furanyl (2-(2,3-dihydro-benzo[b]furanyl), 3-(2,3-dihydro-benzo[b]furanyl), 4-(2,3-dihydro-benzo[b]furanyl), 5 (2,3 dihydro-benzo[b]furanyl), 6-(2,3-dihydro-benzo[b]furanyl), 7-(2,3-dihydro-benzo[b]furanyl), benzo[b]thiophenyl (2-benzo[b]thiophenyl, 3-benzo[b]thiophenyl, 4 benzo[b]thiophenyl, 5 benzo[b]thiophenyl, 6-benzo[b]thiophenyl, 7-benzo[b]thiophenyl), 2,3 dihydro-benzo[b]thiophenyl, (2-(2,3-dihydro-benzo[b]thiophenyl), 3-(2,3-dihydro-benzo[b]thiophenyl), 4-(2,3-dihydro-benzo[b]thiophenyl), 5-(2,3-dihydro-benzo[b]thiophenyl), 6-(2,3-dihydro-benzo[b]thiophenyl), 7-(2,3-dihydro-benzo[b]thiophenyl), indolyl (1-indolyl, 2 indolyl, 3 indolyl, 4-indolyl, 5-indolyl, 6-indolyl, 7-indolyl), indazole (1-indazolyl, 3 indazolyl, 4 indazolyl, 5-indazolyl, 6-indazolyl, 7-indazolyl), benzimidazolyl (1 benzimidazolyl, 2 benzimidazolyl, 4-benzimidazolyl, 5-benzimidazolyl, 6-benzimidazolyl, 7 benzimidazolyl, 8 benzimidazolyl), benzoxazolyl (1-benzoxazolyl, 2-benzoxazolyl), benzothiazolyl (1-benzothiazolyl, 2-benzothiazolyl, 4-benzothiazolyl, 5-benzothiazolyl, 6 benzothiazolyl, 7 benzothiazolyl), carbazolyl (1-carbazolyl, 2-carbazolyl, 3-carbazolyl, 4 carbazolyl), 5H dibenz[b,f]azepine (5H-dibenz[b,f]azepin-1-yl, 5H-dibenz[b,f]azepine-2-yl, 5H dibenz[b,f]azepine-3-yl, 5H-dibenz[b,f]azepine-4-yl, 5H-dibenz[b,f]azepine-5-yl), 10,11 dihydro-5H-dibenz[b,f]azepine (10,11-dihydro-5H-dibenz[b,f]azepine-1-yl, 10,11 dihydro-5H-dibenz[b,f]azepine-2-yl, 10,11-dihydro-5H-dibenz[b,f]azepine-3-yl, 10,11 dihydro-5H-dibenz[b,f]azepine-4-yl, 10,11-dihydro-5H-dibenz[b,f]azepine-5-yl), and the like.

In some embodiments of Structure (I-V), the alkyl, aryl, arylalkyl, heterocyclylalkyl and/or heterocyclylalkyl group is substituted. In this context, "substituted" refers to an alkyl, aryl, arylalkyl, heterocyclyl and/or heterocyclylalkyl group in which one or more bonds to a hydrogen atom are replaced by one or more bonds to a non-hydrogen atom. The alkyl, aryl, arylalkyl, heterocyclyl and/or heterocyclylalkyl group may be mono-substituted, or substituted more than once, such as di-, tri- or higher-substituted. Representative substituents in this regard include, but are not limited to, a halogen (F, Cl, Br or I); an oxygen atom in groups such as hydroxyl groups, alkoxy groups, aryloxy groups, aralkyloxy groups, oxo(carbonyl) groups, carboxyl groups including carboxylic acids, carboxylates, and carboyxlate esters; a sulfur atom in groups such as thiol groups, alkyl and aryl sulfide groups, sulfoxide groups, sulfone groups, sulfonyl groups, and sulfonamide groups; a nitrogen atom in groups such as amines, hydroxylamines, nitriles, nitro groups, N-oxides, hydrazides, azides, and enamines; and other heteroatoms in various other groups. Non-limiting examples of substituents that can be bonded to a substituted carbon (or other) atom include F, Cl, Br, I, OR', OC(O)N(R')$_2$, CN, CF$_3$, OCF$_3$, R', O, S, C(O), S(O), methylenedioxy, ethylenedioxy, N(R)$_2$, SR', SOR', SO$_2$R', SO$_2$N(R')$_2$, SO$_3$R', C(O)R', C(O)C(O)R', C(O)CH$_2$C(O)R', C(S)R', C(O)OR', OC(O)R', C(O)N(R')$_2$, OC(O)N(R')$_2$, C(S)N(R')$_2$, (CH$_2$)$_0$—$_2$NHC(O)R', (CH2)0-2N(R')N(R')$_2$, N(R')N(R')C(O)R', N(R)N(R)C(O)OR', N(R')N(R')CON(R')$_2$, N(R')SO$_2$R', N(R')SO$_2$N(R')$_2$, N(R')C(O)OR', N(R')C(O)R', N(R')C(S)R', N(R')C(O)N(R')$_2$, N(R')C(S)N(R')$_2$, N(COR')COR', N(OR')R', C(=NH)N(R)$_2$, C(O)N(OR')R', or C(=NOR')R' wherein each occurrence of R' is hydrogen or C$_{1-4}$ alkyl. In more specific embodiments, representative substituents include —CN, —OH, —OCH$_3$, —SH, —SCH$_3$, —NH$_2$, CH$_3$, —CH$_2$CH$_3$, —CH$_2$CH$_2$CH$_3$, N$^+$(C$_{1-4}$ alkyl)$_3$, —C(=O)OH, —C(O)NH$_2$, —NHC(=NH)NH$_2$, —OP(=O)(OH)$_2$ and —OS(=O)$_2$OH.

In other embodiments of Structures (I-v), substituted alkyl refers to an alkyl group in which one or more bonds to a hydrogen atom of the alkyl group are replaced by one or more bonds to aryl or heterocyclyl group, wherein such aryl or heterocyclyl group(s) may be further substituted with a substituent as defined in the preceding paragraph.

A "hydrate" is a compound that exists in a composition with water molecules. The composition can include water in stoichiometric quantities, such as a monohydrate or a dihydrate, or can include water in random amounts. As the term is used herein a "hydrate" refers to a solid form (i.e., a compound in water solution, while it may be hydrated, is not a hydrate as the term is used herein).

A "solvate" is a similar composition except that a solvent other that water replaces the water. For example, methanol or ethanol can form an "alcoholate", which can again be stoichiometric or non-stoichiometric. As the term is used herein a "solvate" refers to a solid form (i.e., a compound in solution in a solvent, while it may be solvated, is not a solvate as the term is used herein).

A "homolog" of a compound of the invention is a compound having one or more atoms of the compound replaced by an isotope of such atom. For example, homologs include compounds with deuterium in place of one or my hydrogen atom, such as embodiments wherein a methyl group is fully or partially deuterated (e.g., CD$_3$). Isotopic substitutions which may be made in the formation of homologs of the invention include non-radioactive (stable) atoms such as deuterium and carbon 13, as well as radioactive (unstable) atoms such as tritium, carbon 14, iodine 123, iodine 125, etc.

The term "sphingosine-1-phosphate receptor" or "S1P receptor" as used herein refers to a class of G protein-coupled receptors that share the lipid signalling molecule Sphingosine-1-phosphate (S1P) as a ligand. They are divided into five subtypes: S1PR1 (also referred to as S1P$_1$), S1PR2 (also referred to as S1P$_2$), S1PR3 (also referred to as S1P$_3$), S1PR4 (also referred to as S1P$_4$) and S1PR5 (also referred to as S1P5). Each receptor subtype possesses a unique expression profile and utilizes different signaling systems. Due to this receptor diversity, S1P receptors modulate different physiological functions including, but not limited to, lymphocyte trafficking and blood vessel integrity.

An "S1P receptor agonist" refers to a compound that functions as an agonist to the S1P receptor (as opposed to functioning as an inhibitor). Such compounds can be selective for action on specific subtypes of the S1P receptor family; for example a compound of the invention can act at a lower concentration on subtype 1 of the S1P receptor family than on other subtypes of the S1P receptor family. More specifically, an "S1P agonist" of the invention can selectively act on subtype 1 receptors compared to its action on, for example, subtype 3. In some embodiments, an "S1P receptor agonist may also be selective for other members of the S1P receptor family, such as S1P$_5$.

An "S1P$_1$ agonist" refers to a compound that functions as an agonist to the S1P$_1$ receptor, which may be selective for the S1P$_1$ receptor compared to other S1P receptor subtypes. In some embodiments, an S1P$_1$ agonist is also selective for S1P$_5$.

In one embodiment, the S1P receptor agonist provides therapeutic benefit in the context of relapsing-remitting multiple sclerosis (RRMS), by down-modulating S1P receptor and resulting in retention of autoreactive lymphocytes in secondary lymphoid organs. As set forth in greater detail below, ozanimod activity on immune cell subsets was examined in the experimental autoimmune encephalomyelitis (EAE)-induced mouse model of Multiple Sclerosis (MS). C57BL/6 mice were immunized with MOG35-55 and pertussis toxin to initiate immune cell activation, migration to the spinal cord and neurodegeneration. Animals were treated with oral ozanimod either semi-therapeutically or therapeutically to investigate the impact on peripheral immune cell expansion and migration into the spinal cord. The plasma biomarker of CNS injury, neurofilament light (NfL), was measured at study termination.

As used herein, "treating" refers to an alleviation of symptoms associated with the condition for which S1P receptor-mediated neuroprotection is medically indicated, or inhibition of or slowing further progression or worsening of those symptoms, or prevention or prophylaxis of the condition.

The expression "effective amount" or "therapeutically effective amount", when used to describe use of a compound of the invention in providing treatment for the condition for which S1P receptor-mediated neuroprotection is medically indicated, refers to an amount of the compound that alleviates, in whole or in part, symptoms associated with the conditions, or halts or slows further progression or worsening of those symptoms, or prevents or provides prophylaxis for the condition.

As used herein, "neuroprotection" refers to an effect that may result in salvage, recovery, or regeneration of the nervous system, neurons, neuronal structure, and/or neuronal function. Neuroprotection may reverse, prevent, or slow neuronal cell death resulting from disease or injury.

Conditions for which S1P receptor-mediated neuroprotection are medically indicated include those conditions served by a reduction in spinal cord inflammation, a reduction in spinal cord axial demyelination, a reduction in T cell expansion, a decrease in monocyte infiltration into the spinal cord, limiting microglia expansion into the spinal cord, a reduction in MAO-B activity, an increase in AKT and/or ERK activity, or any combination thereof. In this context, "served" means that the condition is medically benefited, such as by alleviating, in whole or in part, symptoms associated with the conditions, or halting or slowing further progression or worsening of those symptoms, or preventing or providing prophylaxis for the condition Conditions for which S1P receptor-mediated neuroprotection are medically indicated include: Parkinson's disease, Huntington disease, amyotrophic lateral sclerosis (ALS), Alzheimer's disease, multiple sclerosis (primary progressive and/or secondary progressive), Rett syndrome, and/or muscular dystrophy. In a further embodiment, the condition for which S1P receptor-mediated neuroprotection is medically indicated is served by a reduction in brain volume loss.

Methods are provided herein for treating certain conditions for which S1P receptor-mediated neuroprotection are medically indicated, including Parkinson's disease, Huntington disease, amyotrophic lateral sclerosis (ALS), Alzheimer's disease, multiple sclerosis (primary progressive and/or secondary progressive), Rett syndrome, and/or muscular dystrophy, comprising administering to the patient a therapeutically effective amount of a S1P receptor agonist as described above.

Parkinson's disease is a progressive, neurodegenerative disorder that predominantly affects dopaminergic neurons in the substantia nigra area of the brain. As the neurons in the substantia nigra degenerate, the reduction in dopamine causes abnormal neural activity that results in a chronic, progressive deterioration of motor function control. Symptoms include muscle rigidity, tremors, slowness, impaired balance, and changes in speech and gait. Other symptoms may include anxiety, depression, and dementia.

The effect of a S1P receptor agonist can be assessed in a mouse model of Parkinson's disease. The MitoPark mouse is a mouse model of Parkinson's disease having mitochondrial transcription factor A inactivated in dopamine neurons. MitoPark mice exhibit several features of Parkinson's disease, such as adult-onset degeneration of nigrostriatal dopamine circuitry; motor deficits that are ameliorated by L-DOPA administration; progressive course of phenotypic manifestations and neurodegeneration; and altered response to L-DOPA treatment dependent on disease stage. A neurotoxin-based mouse model of Parkinson's disease is created by administering the mitochondrial complex-I inhibitor rotenone to mice. Methods that can be used to determine effects of treatment with the S1P receptor agonist on Parkinson's disease include measures of striatal tyrosine hyroxylase positive (TH+) neurons, a marker for dopaminergic neurons, and assessment of locomotor activity.

Huntington disease is an inherited disorder that causes the progressive degeneration of neurons in the in the caudate and putamen of the brain. Symptoms include chorea, dystonia, incoordination, athetosis, cognitive decline, and behavioral difficulties. Huntington disease is caused by a trinucleotide expansion of a CAG repeat in exon 1 of the huntingtin gene. The mutant huntingtin gene forms insoluble aggregates that accumulate in the cytoplasm and nucleus of neurons.

The effect of a S1P receptor agonist can be assessed in a mouse model of Huntington disease. R6/2 mouse expresses exon 1 of the human huntingtin gene containing 150 CAG repeats and develops neurological symptoms that resemble many of those seen in Huntington disease. Mice expressing A53T mutation to α-synuclein develop severe movement disorders. Methods that can be used to determine effects of treatment with the S1P receptor agonist on Huntington disease include measures of survival locomotor activity, brain derived neurotrophic factor (BDNF) expression levels, and brain weight.

Amyotrophic lateral sclerosis (ALS), also known as motor neuron disease (MND), and Lou Gehrig's disease, is caused by the progressive degeneration of motor neurons in the spinal cord and brain. Symptoms include muscle stiffness or weakness, muscle atrophy, muscle twitching, loss of control of voluntary movement, and difficulty breathing.

The effect of a S1P receptor agonist can be assessed in a mouse model of ALS. mSOD1-G93A mouse expresses a mutant superoxide dismutase 1 (SOD1) develop normal into adulthood and then display motor impairments at about 90-100 days of age. Methods that can be used to determine effects of treatment with the S1P receptor agonist on ALS include measures of survival, disease score, locomotor activity, and BDNF expression levels.

Alzheimer's disease is a progressive neurodegenerative disorder whose early symptoms include mild memory loss, executive function, agnosia, apraxia. As the disease progresses, the patient experiences long term memory loss, loss of coordination, behavioral and neuropsychiatric changes, difficulty with language, and confusion. The cause of most disease cases is not usually known, though genetic factors, extracellular amyloid beta ($A_\beta$) deposits, and formation neurofibrillary tangles may play a role.

The effect of a S1P receptor agonist can be assessed in a mouse model of Alzheimer's disease. The 5xFAD mouse is an amyloid plaque transgenic mouse model that exhibits accumulation of intraneuronal $A\beta_{42}$ prior to plaque formation. The SXFAD mouse expresses amyloid precursor protein with K670N/M671L (Swedish mutation), I716V (Florida mutation), and V717I (London mutation), and presenilin 1 with M146L and L286V mutations. Individually, each FAD mutation enhances $A\beta_{42}$ generation, but together they act synergistically in the transgenic mouse to predominantly make $A\beta_{42}$. As a result, SXFAD mice represent a very aggressive amyloid deposition model that develops intraneuronal $A\beta_{42}$ at 1.5 months, plaques at 2 months, memory deficits at 4 months, and neuron loss at 9 months of age. Methods that can be used to determine effects of treatment with the S1P receptor agonist on Alzheimer's disease include measuring Aβ levels, and measuring activated microglia.

Multiple sclerosis is an autoimmune disease of the brain and spinal cord wherein the immune system attacks the myelin sheath. Multiple sclerosis can cause many different symptoms, including vision loss, pain, fatigue, impaired coordination, bladder and bowel problems, tingling, numbness, and loss of muscle control. Most multiple sclerosis patients have relapsing-remitting multiple sclerosis (RRMS), where the initial appearance of symptoms are followed by clearly defined attacks of new or increasing neurologic symptoms, called relapses, which are followed by periods of partial or complete recovery (remissions). Secondary progressive multiple sclerosis (SPMS) follows an initial relapsing-remitting course, which eventually transitions to a progressive worsening of neurologic function over time. Symptoms begin to cintue steadily without relapses or remissions. Primary progressive multiple sclerosis (PPMS) is characterized by worsening neurologic function from the onset of symptoms, without early relapses or remissions.

The effect of a S1P receptor agonist can be assessed in mouse models of multiple sclerosis. The TMEV mouse is is a model of primary progressive multiple sclerosis. Infection of mice with Theiler's murine encephalomyelitis virus (TMEV) induces inflammatory demyelination and axonal degeneration in the spinal cord. Experimental autoimmune encephalomyelitis (EAE) induced in ABH Biozzi mouse is a model of secondary progressive multiple sclerosis. Methods that can be used to determine the effects of treatment with the S1P receptor agonist on PPMS or SPMS include measuring disease score, locomotor activity, and histological analysis.

Rett Syndrome is a non-inherited, post-natal, genetic neurological disorder that primarily affects females and is caused by mutations on the X chromosome in the MECP2 gene. Symptoms of Rett Syndrome include decreased or loss of use of fine motor skills, decreased or loss of verbal speech, abnormal gait, stereotypic hand movements. Other symptoms may include breating disturbances while awake, bruxism while awake, impaired sleep pattern, abnormal muscle tone, scoliosis, growth retardation, peripheral vasomotor disturbances, small cold hands and feet, inappropriate laughing/screaming spells, diminished response to pain, and intense eye communication.

The effect of a S1P receptor agonist can be assessed in a mouse model of Rett Syndrome. MECP2 null mice and mice in which MECP2 was deleted in the brain show neurological symptoms that mimic Rett syndrome. Methods that can be used to determine effects of treatment with the S1P receptor agonist on Rett Syndrome include measures of survival, locomotor activity, and brain derived neurotrophic factor (BDNF) expression levels.

Muscular dystrophy is a group of inherited diseases that cause progressive weakness and loss of muscle mass. The disorders differ in which muscles are primarily affected, the degree of weakness, how fast they worsen, and when symptoms begin. Symptoms may include progressive muscle wasting, poor balance, scoliosis, progressive inability to walk, waddling gait, calf deformation, limited range of movement, difficulty breathing, cardiomyopathy, muscle spasms, and Gowers' sign. Examples of muscular dystrophy include Becker muscular dystrophy, congenital muscular dystrophy, Duchenne muscular dystrophy, distal muscular dystrophy, Emery-Dreifuss muscular dystrophy, Facioscapulohumeral muscular dystrophy, Limb-girdle muscular dystrophy, myotonic muscular dystrophy, and Oculopharyngeal muscular dystrophy.

The effect of a S1P receptor agonist can be assessed in a mouse model of muscular dystrophy. The MDX mouse MDX mouse on DBA/2J background and γ-sarcoglycan null mice on DBA/2J background (Sgcg−/− DBA/2J mouse) are mouse models of Duchenne muscular dystrophy. Methods that can be used to determine effects of treatment with the S1P receptor agonist on muscular dystrophy include measures of myofiber permeability and muscle fibrosis.

The effect of a S1P receptor agonist on spinal cord inflammation can be assessed by measuring levels of pro-inflammatory cytokines and chemokines in the cerebrospinal fluid, such as TNF-α, IL-6, IL-1β, and CXCL13. Assays for determining gene expression are well known in the art, and include, for example, quantitative PCR, gene expression microarray, Northern blot, RNA sequencing, immunoassay based detection. Plasma neurofilament light chain (NfL) level may also be used as an indicator of spinal cord inflammation.

The effect of a S1P receptor agonist on spinal cord axial demyelination or reduction in axonal breaks can be assessed by measuring concentration of neurofilament light chain (NfL) in the plasma. NfL is released to the plasma following axonal injury and degeneration. Histological examination of axons with antineurofilament H non-phosphorylated mouse antibody SMI-32 can also be used to assess axonal demyelination or breaks. NfH is phosphorylated in healthy axons and unphosphorylated in damaged axons.

Flow cytometric analysis can be used to assess the effects of a S1P receptor agonist on T cell expansion in peripheral blood or into the spinal cord; monocyte infiltration into the spinal cord, or microglia expansion into the spinal cord.

The effect of a S1P receptor agonist on reduction in brain volume loss can be measured using magnetic resonance imaging in conjunction with various quantification algorithms, such as brain boundary shift integral, robust boundary shift integral, FreeSurfer, SIENA, SIENAX, and Jacobian integration ( The effect of a S1P receptoragonist on MAO-B activity can be assessed by measuring the inhibition of conversion of substrate kynuramine to 4-hydroxyquinoline as described in Example 4.

The effect of a S1P receptor agonist on AKT or ERK activity in astrocytes can be assessed by measuring activity levels of AKT or ERK. AKT or ERK activity can be detected by measuring AKT or ERK phosphorylation, using phosphoprotein immunoassays, or measuring AKT or ERK kinase activity, using kinase assays known in the art.

EXAMPLES

General Synthetic Procedures:

$^1$H NMR (400 MHz) and $^{13}$C NMR (100 MHz) were obtained in solution of deuteriochloroform (CDCl$_3$), deuteriomethanol (CD$_3$OD) or dimethyl sulfoxide—D$_6$ (DMSO). NMR spectra were processed using Mestrec 5.3.0 and 6.0.1. $^{13}$C NMR peaks that are bracketed are two rotomers of the same carbon. Mass spectra (LCMS) were obtained using an Agilent 1100/6110 HPLC system equipped with a Thompson ODS-A, 100 A, 5µ (50×4.6 mm) column using water with 0.1% formic acid as the mobile phase A, and acetonitrile with 0.1% formic acid as the mobile phase B. The gradient was 20-100% with mobile phase B over 2.5 min then held at 100% for 2.5 mins. The flow rate was 1 mL/min. For more hydrophobic compounds, the following gradient was used, denoted as Method 1: 40-95% over 0.5 min, hold at 95% for 8.5 min, then return to 40% over 2 min, with a flow rate of 1 mL/min. Final compounds were checked for purity using Method 2: 5% for 1 min, 5-95% over 9 min, then hold at 95% for 5 min, with a flow rate of 1 mL/min. Enantiomeric excess was determined by integration of peaks that were separated on a Chiralpak AD-H, 250×4.6 mm column, 5 μm particle size. Flow rate of 1 mL/min and an isocratic mobile phase. Unless otherwise indicated, the chiral data provided uses this method. Alternatively, chiral separations were performed under the following conditions, denoted as Chiral Method 1: Chiralpak AY-H, 250×4.6 mm column, 5 μm particle size. Flow rate of 1 mL/min and an isocratic mobile phase. Chiral Method 2: Chiralcel OZ-3, 250×4.6, 3 μm particle size at a flow rate of 0.75 ml/min. The pyridine, dichloromethane (DCM), tetrahydrofuran (THF), and toluene used in the procedures were from Aldrich Sure-Seal bottles kept under nitrogen ($N_2$). All reactions were stirred magnetically and temperatures are external reaction temperatures. Chromatographies were carried out using a Combiflash Rf flash purification system (Teledyne Isco) equipped with Redisep (Teledyne Isco) silica gel ($SiO_2$) columns. Preparative HPLC purifications were done on Varian ProStar/PrepStar system using water containing 0.05% trifluoroacetic acid as mobile phase A, and acetonitrile with 0.05% trifluoroacetic acid as mobile phase B. The gradient was 10-80% with mobile phase B over 12 min, hold at 80% for 2 min, and then return to 10% over 2 min with flow rate of 22 mL/min. Other methods similar to this may have been employed. Fractions were collected using a Varian Prostar fraction collector and were evaporated using a Savant SpeedVac Plus vacuum pump. Microwave heating was performed using a Biotage Initiator microwave reactor equipped with Biotage microwave vessels. The following abbreviations are used: ethanol (EtOH), carbonyldiimidazole (CDI), isopropanol (IPA), and 4-dimethylaminopyridine (DMAP).

Example 1

Synthesis of Representative Compounds

The compounds disclosed herein may be made according to the following examples and by known techniques, including those disclosed in U.S. Pat. No. 8,362,048 (incorporated herein by reference in its entirety). For example, synthesis of the following compound (R and S form) is as disclosed in U.S. Pat. No. 8,362,048:

Similarly, synthesis of the following compounds (R and S forms) is as disclosed in U.S. Pat. No. 8,362,048:

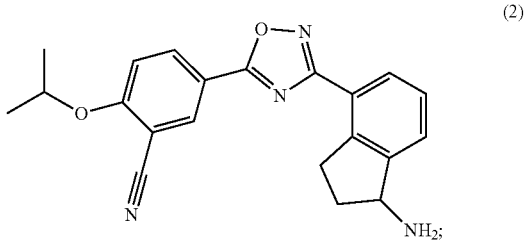

(2)

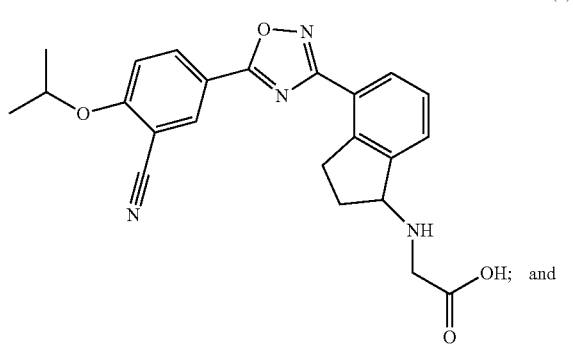

(3)

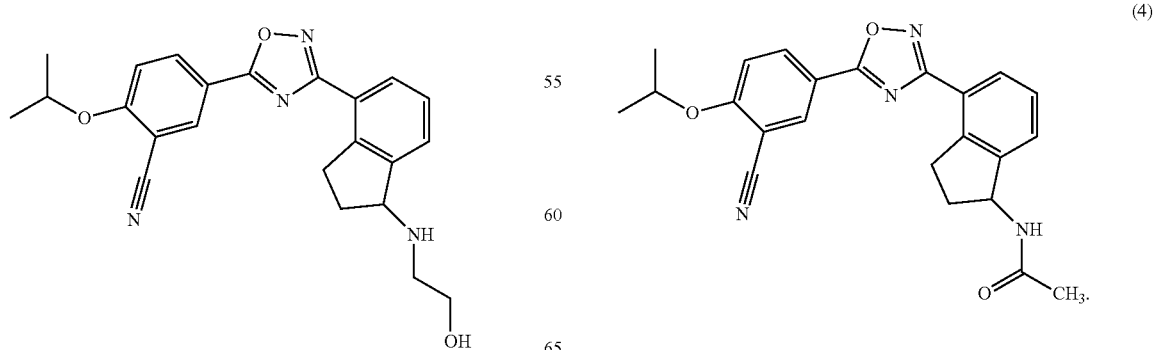

Synthesis of compound (1) may be accomplished by the following synthetic scheme.

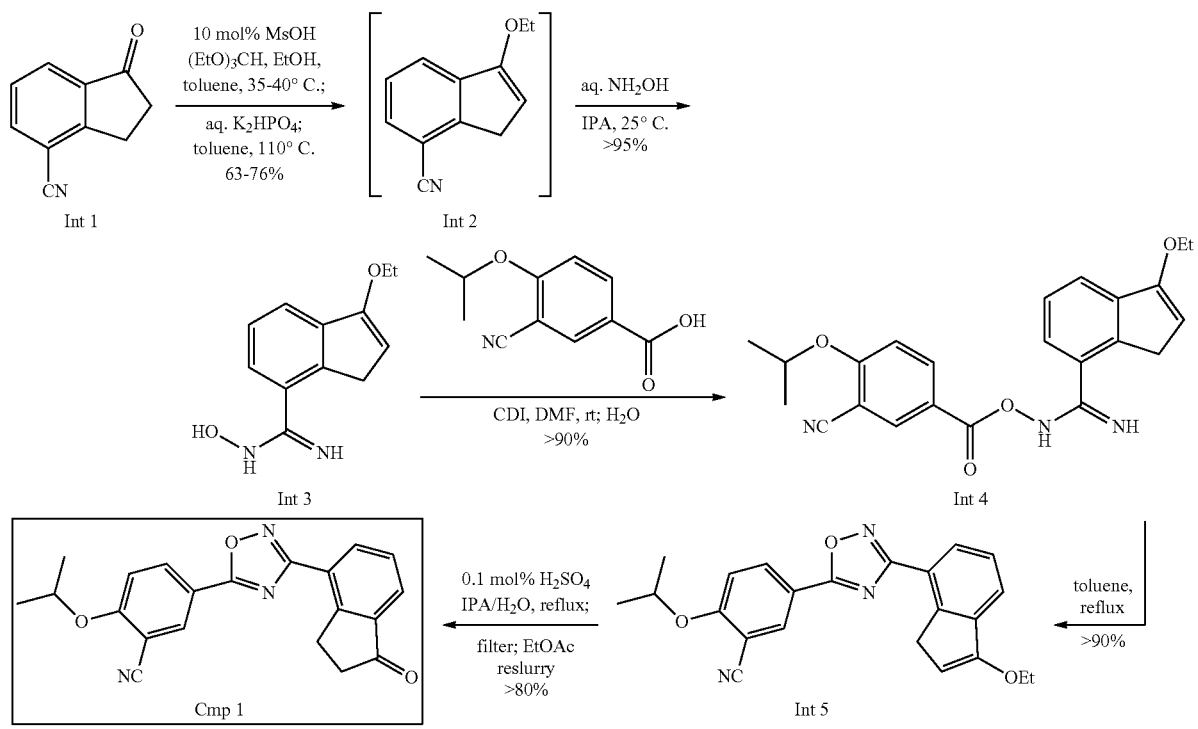

Step 1—Synthesis of 3-ethoxy-1H-indene-7-carbonitrile (Int 2)

A stirred mixture of 1-oxo-2,3-dihydro-1H-indene-4-carbonitrile (Int 1) (20.0 g, 98 wt %, 18.6 assay g, 124.8 mmol) in abs EtOH (20 mL), triethylorthoformate (80 mL, 481 mmol) and methanesulfonic acid (0.88 mL, 12.5 mmol) in toluene (80 mL) was heated at 43-47° C. After 1 h, GC analysis showed orthoformate consumed and 12.8 area % of Int 1 remaining. A further charge of triethylorthoformate (20 mL, 120.2 mmol) was made and after 45 min GC analysis showed 1.5 area % Int 1. The batch was cooled to ambient temperature and then poured into 1 M aq. $K_2HPO_4$ (200 mL) with vigorous stirring while maintaining a quench temperature <15° C. The two-phase mixture was vigorously stirred for 10 min. The phases were separated and the aqueous phase (pH 11) was back extracted with toluene (100 mL). The organic phases were combined and distilled at atmospheric pressure to remove 340 mL distillate. Toluene was added (500 mL) and distilled at atmospheric pressure to remove 500 mL distillate. Total distillation time 3 h, temperature range 80-120° C. At this point the batch was stored overnight at <5° C. Excess orthoformate was removed by chasing with ethyl acetate (100 mL) under reduced pressure until distillation stopped. Another volume of ethyl acetate (100 mL) was added and then concentrated under reduced pressure until distillation stopped. A third volume of ethyl acetate (100 mL) was added and then concentrated under reduced pressure until distillation stopped, after which GC analysis confirmed no orthoformate remaining. The crude was then stirred at 110° C. for 1 h, to convert the intermediate ketal to 3-ethoxy-1H-indene-7-carbonitrile (Int 2). Upon cooling, the crude (mobile oil, 21.34 g) was assayed for Int 2 by $^1$H NMR employing mesitylene as an internal standard. The oil assayed at 78.1 wt % product=16.73 assay g, 90.0 mmol=72.1% assay yield. The crude oil was then purified by filtration through a silica gel plug eluting with 15% EtOAc/hexane. The pure fractions were combined and utilized for the next step. $^1$H NMR (400 MHz, $d_6$-DMSO) δ 7.78 (d, J=8.4, 1H), 7.63 (m, 1H), 7.49 (m, 1H), 5.60 (m, 1H), 1.38 (t, J=6.8 Hz, 1H), 1.19 (t, J=6.8 Hz, 1H); LRMS: calcd for $C_{12}H_{12}NO^+$[M+H]: 186.2; Found: 186.2.

Step 2—Synthesis of Int 3

An EtOAc/hexane solution (650 mL) of 3-ethoxy-1H-indene-7-carbonitrile (Int 2) is concentrated under reduced pressure to ~17 mL and isopropyl alcohol (IPA, 40 mL) was added. The solution was concentrated to ~17 mL, and a second volume of IPA (34 mL) was added. To the stirred solution was added aqueous hydroxylamine (50%, 30 mL, 455 mmol). The batch was then warmed at 35-40° C. for 5 h, and then stirred at ambient temperature overnight. The batch was cooled to 0° C., seeded (50 mg), and stirred for 30 min for a seed bed to develop. Water (250 mL) was then added dropwise over ~1.5 h. The batch was stirred for 1 h at 0-20° C. The product was isolated by filtration, cake-washed with water (100 mL) and dried on the filter under vacuum and a nitrogen atmosphere, to afford 3-ethoxy-N-hydroxy-1H-indene-7-carboximidamide (Int 3) (20.8 g, 90% yield). $^1$H NMR (400 MHz, $d_6$-DMSO) δ 9.61 (s, 1H), 7.43 (m, 1H), 7.32 (m, 2H), 5.77 (s, 1H), 5.41 (s, 1H), 4.08 (q, J=6.8 Hz, 2H), 3.45 (s, 2H), 1.39 (t, J=6.8 Hz, 3H); LRMS: calcd for $C_{12}H_{15}N_2O_2^+$ [M+H]: 219.2; Found: 219.1.

Step 3—Synthesis of N-((3-cyano-4-isopropoxybenzoyl)oxy)-3-ethoxy-1H-indene-7-carboximidamide (Int 4)

A mixture of CDI (16.64 g, 102.6 mmol) and 3-cyano-4-isopropoxyl benzoic acid (21.06 g 102.6 mmol) in DMF (83 mL) was stirred at 20° C. for 1 h. A solution of 3-ethoxy- N-hydroxy-1H-indene-7-carboximidamide (Int 3) (20.8 g, 93.3 mmol) in DMF (40 mL) was added through an addition funnel over ~5 min. After ~30 min the batch became viscous and a further volume of DMF (40 mL) was added to aid stirring. At this point HPLC assay indicated that the reaction was complete. The resulting slurry was diluted with water (1.5 L), cooled to 0° C., and isolated by filtration. The filter cake was washed with water (1.5 L) and the product dried on the filter under nitrogen flow to afford N-((3-cyano-4-isopropoxybenzoyl)oxy)-3-ethoxy-1H-indene-7-carboximidamide (Int 4) as an off white solid (34.8 g, 90% yield). $^1$H NMR (400 MHz, d$_6$-DMSO) δ 8.70 (s, 1H), 8.33 (d, J=6.8 Hz, 1H), 7.45 (m, 4H), 7.10 (m, 2H), 5.49 (s, 1H), 4.94 (m, 1H), 4.10 (q, J=6.8 Hz, 2H), 3.55 (s, 2H), 1.38 (m, 9H); LRMS: calcd for $C_{23}H_{24}N_3O_4^+$[M+H]: 406.4; Found: 406.2.

Step 4—Synthesis of 5-(3-(3-ethoxy-1H-inden-7-yl)-1,2,4-oxadiazol-5-yl)-2-isopropoxybenzonitrile (Int 5)

N-((3-Cyano-4-isopropoxybenzoyl)oxy)-3-ethoxy-1H-indene-7-carboximidamide (Int 4) (34.8 g, 83.97 mmol) was suspended in toluene (590 mL) and heated to reflux with a Dean-Stark apparatus for 18 h. ~2 mL were collected (theory 1.5 mL). The batch was cooled to ambient temperature, filtered through Celite, and concentrated under vacuum. The crude solid 5-(3-(3-ethoxy-1H-inden-7-yl)-1,2,4-oxadiazol-5-yl)-2-isopropoxybenzonitrile (Int 5) (30 g, 90% yield) is taken as is to the next step. LRMS: calcd for $C_{23}H_{22}N_3O_3^+$ [M+H]: 388.4; Found: 388.3.

Step 5—Synthesis 2-isopropoxy-5-(3-(1-oxo-2,3-dihydro-1H-inden-4-yl)-1,2,4-oxadiazol-5-yl)benzonitrile (Cpd. No. 1)

Int 5 (30 g, 75.57 mmol) is suspended in 4:1 IPA/H$_2$O (300 mL). Catalytic H$_2$SO$_4$ (0.1 mL, 0.19 mmol) is added, and the resulting mixture is heated to reflux for 12 h. The slurry is cooled to ambient temperature and stirred for 1 h. The product is isolated by filtration and washed with 4:1 IPA/H$_2$O (100 mL). After drying on the filter for 1 h under vacuum, the wet cake is charged back to the reactor and suspended in EtOAc (300 mL). The mixture is heated to reflux for 3 h, then cooled to ambient temperature and stirred for 1 h. The slurry is filtered, washed with EtOAc (100 mL), and dried on the filter under nitrogen to afford 2-isopropoxy-5-(3-(1-oxo-2,3-dihydro-1H-inden-4-yl)-1,2,4-oxadiazol-5-yl)benzonitrile (Cpd. No. 1) (22 g, 80% yield) as an off-white solid. $^1$H NMR (400 MHz, d$_6$-DMSO) δ 8.55 (d, J=2.0 Hz, 1H), 8.44 (m, 2H), 7.88 (d, J=7.6 Hz, 1H), 7.69 (t, J=7.6 Hz, 1H), 7.57 (d, J=9.2 Hz, 1H), 4.99 (h, J=12.4 Hz, 1H), 3.46 (dd, J$_1$=5.6, J$_2$=11.2 Hz, 2H), 2.76 (dd, J$_1$=5.6, J$_1$=11.2 Hz, 2H), 1.45 (d, J=12.4 Hz, 6H); $^{13}$C NMR (100 MHz, d$_6$-DMSO) δ 205.9, 173.4, 167.4, 162.6, 154.2, 138.1, 134.7, 134.2, 133.9, 128.2, 125.9, 124.5, 115.8, 115.3, 114.9, 102.5, 72.6, 35.9, 27.3, 21.5; LRMS: calcd for $C_{21}H_{18}N_3O_3^+$ [M+H]: 360.1; Found: 360.2; C,H,N Analysis: Found: % C: 70.25, % H: 4.69; % N: 11.71; Theory: % C: 70.18; % H: 4.77; % N: 11.69.

Compounds of Structure (I) may be prepared according to the following synthetic scheme:

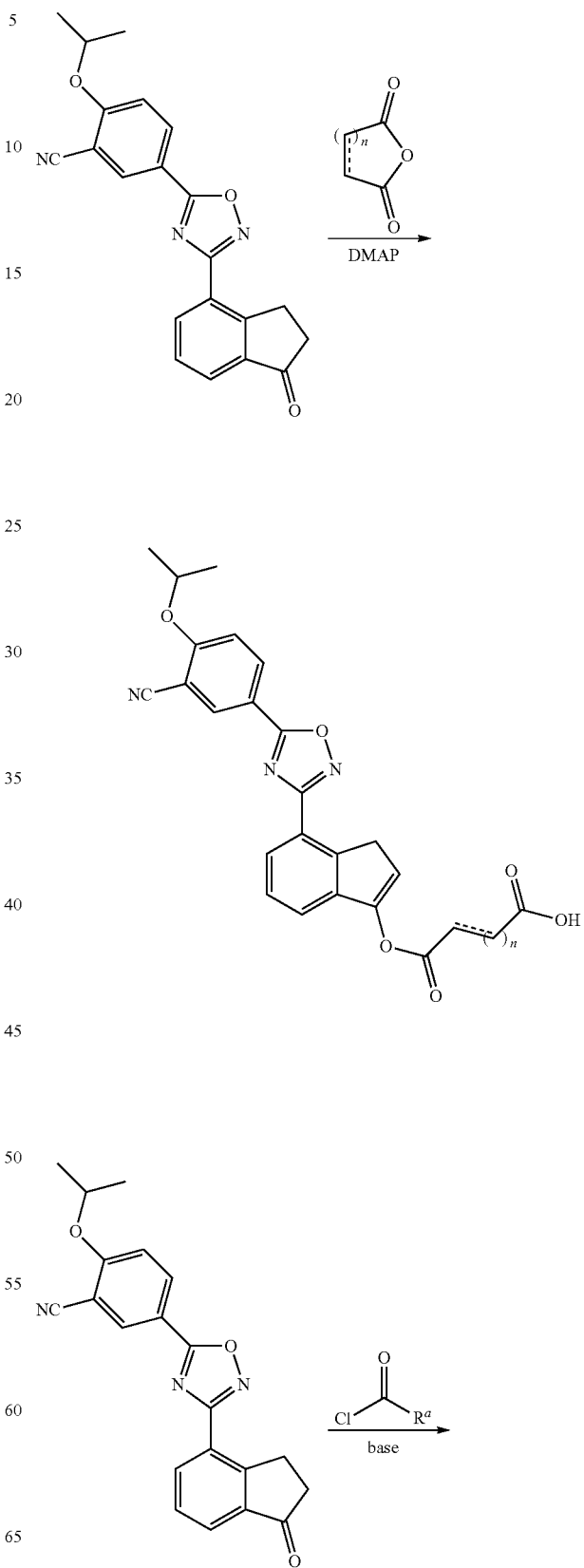

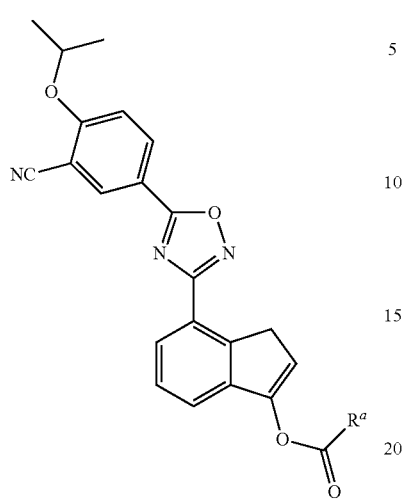

Compounds of Structure (I) can be synthesized starting from Compound 1. Treatment with cyclic anhydrides in the presence of a catalyst like DMAP affords compounds of Structure (I). In addition, generation of compounds of Structure (I) can be achieved by treatment of Compound 1 with a strong base followed by trapping with an acid chloride.

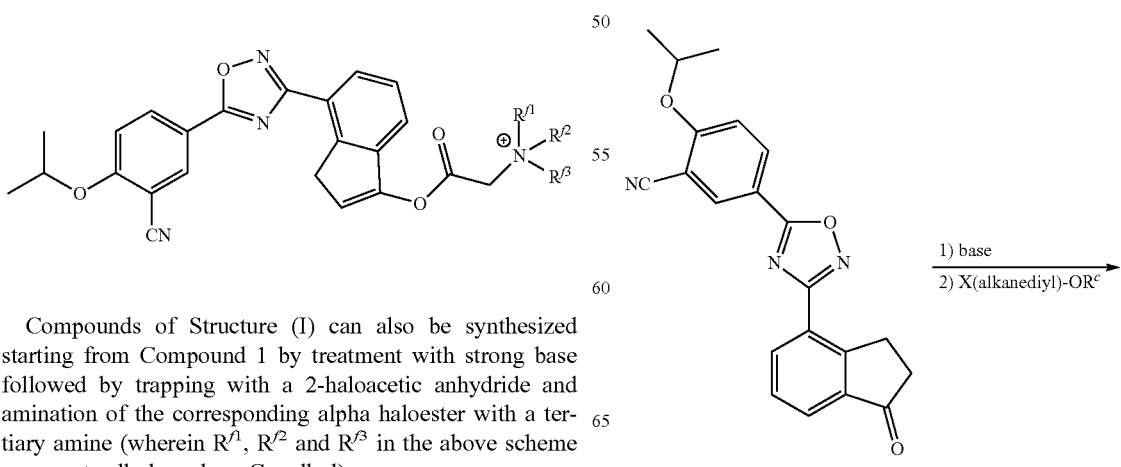

Compounds of Structure (I) can also be synthesized starting from Compound 1 by treatment with strong base followed by trapping with a 2-haloacetic anhydride and amination of the corresponding alpha haloester with a tertiary amine (wherein $R^{f1}$, $R^{f2}$ and $R^{f3}$ in the above scheme represents alkyl, such as $C_{1-4}$alkyl).

Compounds of Structure (II) may be prepared according to the following synthetic scheme:

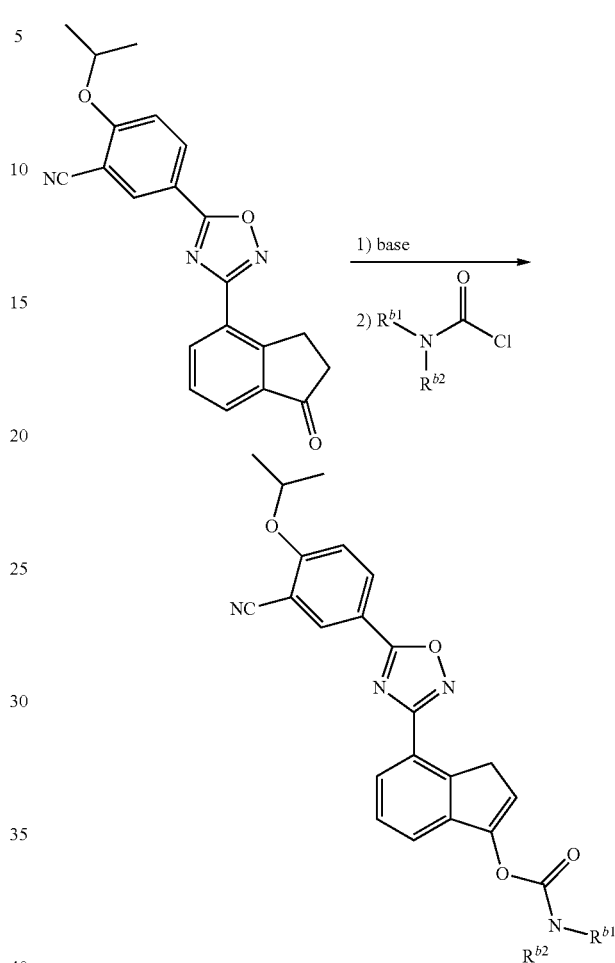

As shown above, compounds of Structure (II) can be synthesized from Compound 1 by treatment with strong base followed by trapping the corresponding enolate with a carbamic chloride.

Compounds of Structure (III) may be prepared according to the following synthetic scheme:

-continued

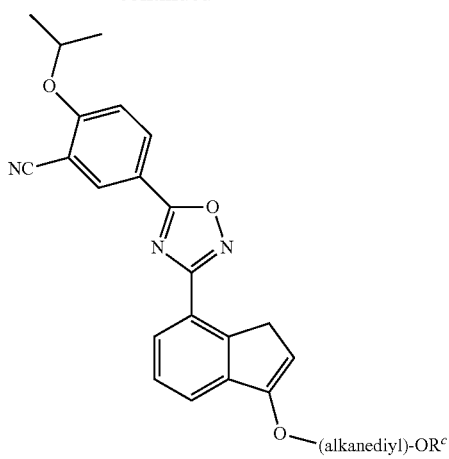

Referring to the above scheme, compounds of Structure (III) can be synthesized starting from Compound 1 by treatment with strong base followed by trapping the corresponding enolate with alkyl halides.

Compounds of Structure (IV) may be prepared according to the following synthetic scheme:

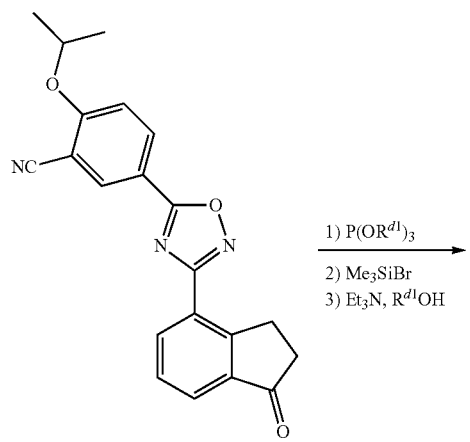

-continued

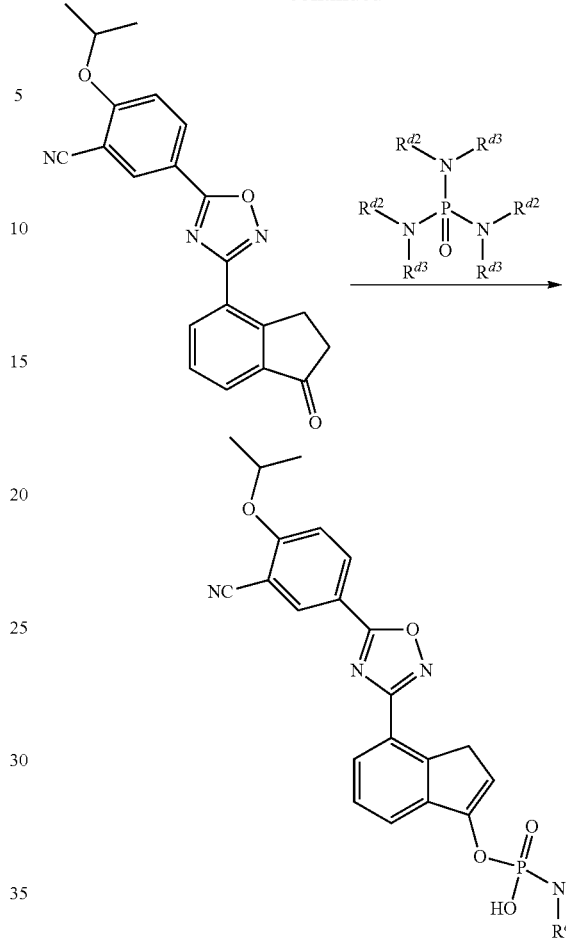

Compounds of Structure (IV) can be synthesized starting from Compound 1 by treatment of with a trialkyl phosphite followed by trimethylsilylbromide to afford the corresponding silyl ester, which is then treated with an alcohol in triethyl amine. Direct treatment of Compound 1 with hexaalkylphosphoric triamides followed by water affords phosphoramides of Structure (IV).

Compounds of Structure (V) may be prepared according to the following synthetic scheme:

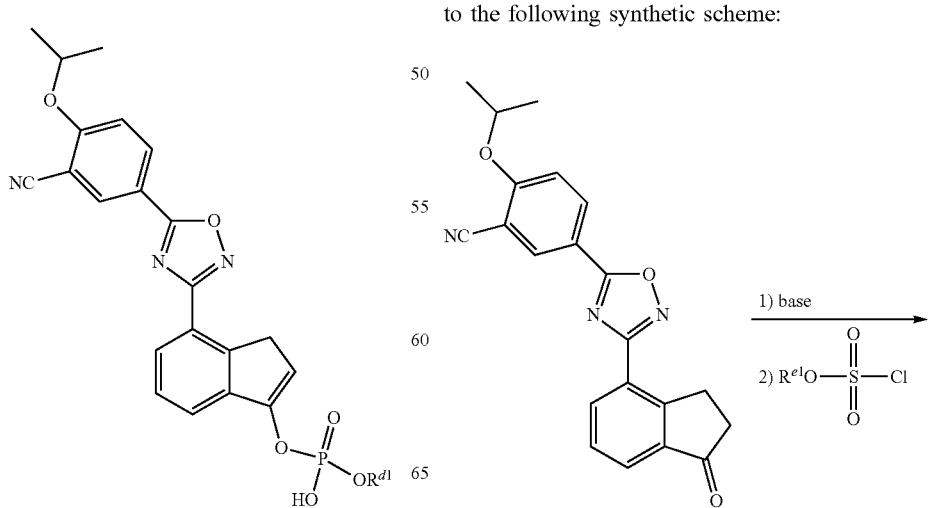

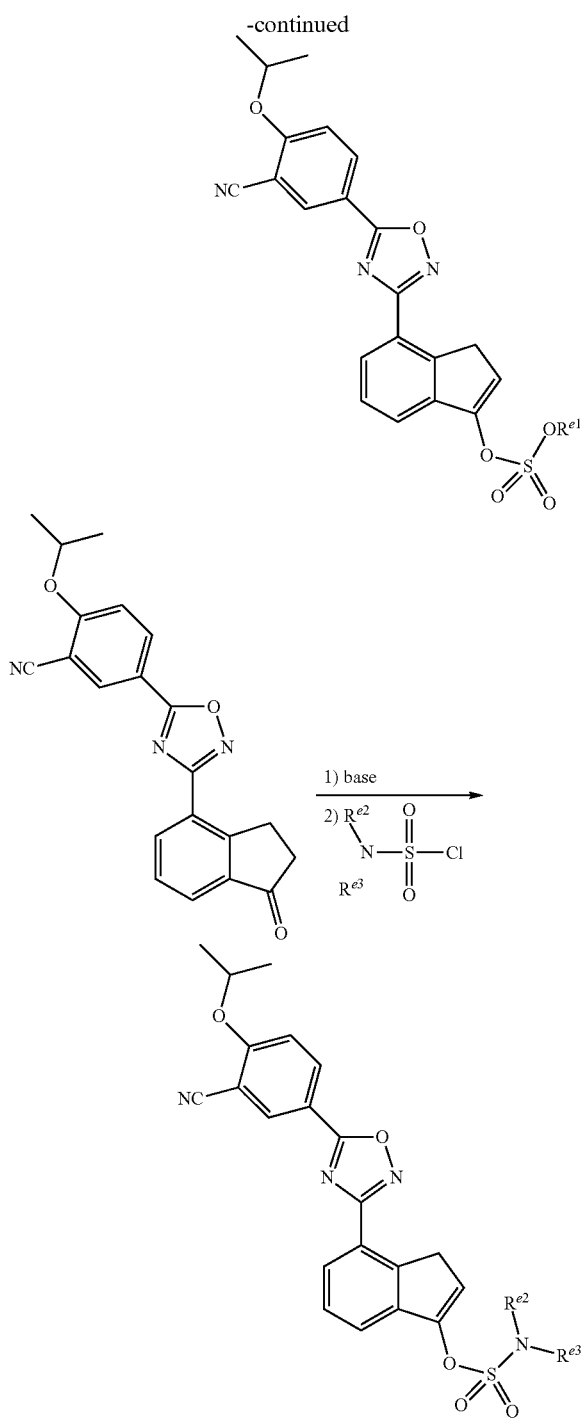

Namely, compounds of Structure (V) can be synthesized starting from Compound 1 by treatment with base followed by chlorosulfuric acid or the corresponding esters. Sulfamates of Structure (V) are afforded by treatment with base followed by sulfamoyl chlorides.

Example 2

Neuroprotection Activity of Ozanimod and Compound (2-R)

Ozanimod activity on immune cell subsets was examined in the experimental autoimmune encephalomyelitis (EAE)-induced mouse model of Multiple Sclerosis (MS). C57BL/6 mice were immunized with MOG35-55 and pertussis toxin to initiate immune cell activation, migration to the spinal cord and neurodegeneration. Animals were treated with oral ozanimod either semi-therapeutically or therapeutically to investigate the impact on peripheral immune cell expansion and migration into the spinal cord. The plasma biomarker of CNS injury, neurofilament light (NfL), was measured at study termination.

Ozanimod was found to reduce spinal cord inflammation and demyelination in EAE. Furthermore, the plasma biomarker of CNS injury NfL decreases with therapeutic dosing of ozanimod (vehicle=3298±350 pg/ml, ozanimod=2209±393 pg/ml, p=0.05). In the EAE model, IFN$\gamma^+$ Th1 and IL-17A$^+$ Th17 T cells and monocytes expand in the periphery between days 7-14 and migrate into the spinal cord between days 14-18 post-immunization. Ozanimod diminishes Th1 and Th17 cell expansion in the periphery by 60-70%, and reduces the number of Th1 and Th17 cells in the spinal cord by ≥80%. In addition to T cells, ozanimod decreases monocyte infiltration into the spinal cord by 65%. Furthermore, microglia expand in the spinal cord day 18-21 post-immunization and mice treated with ozanimod reduced microglia expansion by 75%.

Accordingly, ozanimod reduces the peripheral expansion of Th1 and Th17 T cell subsets and results in a significant reduction in both subsets migrating into the spinal cord. Furthermore, migrating monocytes and expanding resident microglia are reduced with ozanimod treatment. Together, this data demonstrates that ozanimod directly modulates and reduces immune cells that drive CNS inflammation and neurodegeneration in a mouse model of MS.

In addition, the effects of ozanimod on the CNS were examined in vivo using the cuprizone-induced mouse model of demyelination and in vitro in primary rodent astrocytes. Efficacy of ozanimod or compound (2-R) was examined in the cuprizone-induced mouse model of neuroprotection. C57BL/6 mice were treated with cuprizone (0.3% weight/weight orally) and rapamycin (10 mg/kg intraperitoneally daily) to demyelinate axons in the brain and concurrently treated with ozanimod (0.1, 0.3, or 1 mg/kg) or compound (2-S) (1 mg/kg) by daily oral gavage to investigate its neuroprotective activity. Neuroprotection was assessed through examination of axonal pathology in the corpus callosum using SMI-32 (antineurofilament H non-phosphorylated mouse monoclonal antibody) staining, functional assessment through kinematic gait analysis and the plasma biomarker neurofilament light chain (NfL). Further, direct activity of ozanimod was examined in resting and activated primary rodent astrocytes in vitro.

Figure 2:
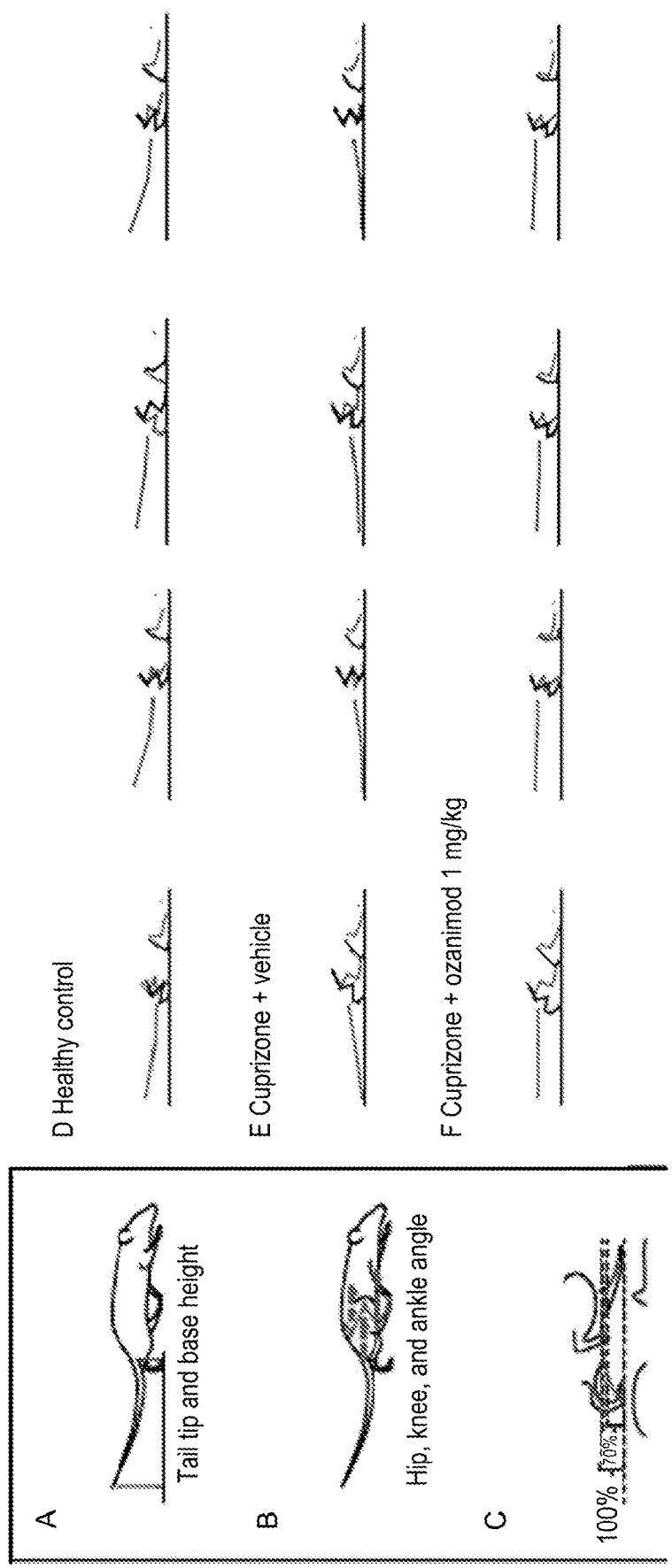
FIGS. 2A-F shows that ozanimod (1 mg/kg) improved kinematic gait in cuprizone-induced demyelinated mice compared with vehicle. The altered gait parameters in vehicle-treated mice that significantly improved in ozanimod treated mice included tail tip height (FIG. 2A), hip orientation, knee/ankle function (FIG. 2B), and lower forelimb paw trajectory (FIG. 2C). Kinematic gait tracings for healthy naïve control (FIG. 2D), cuprizone+vehicle-treated (FIG. 2E), and cuprizone+ozanimod-treated (FIG. 2F) mice are shown.
Figure 3:
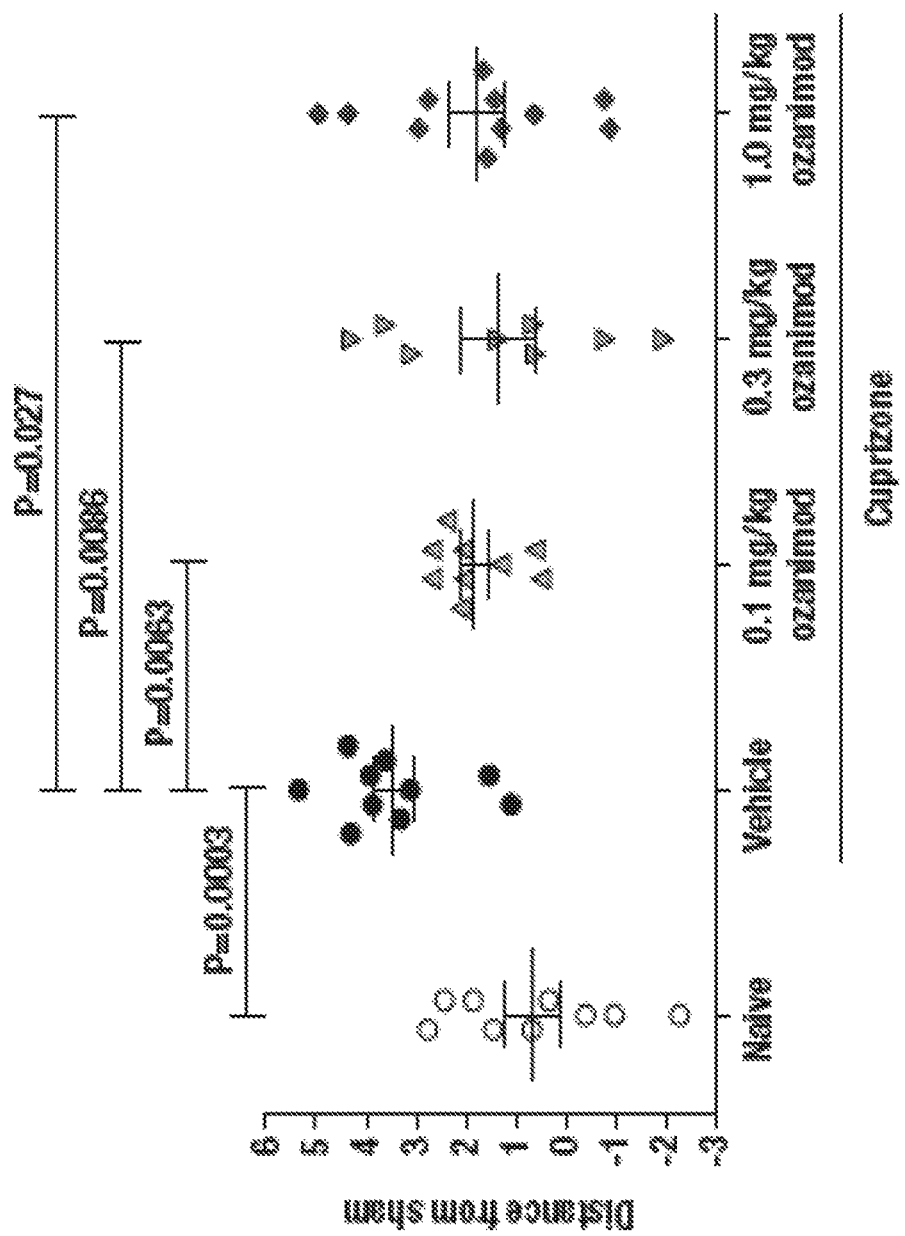
FIG. 3 shows that addition of ozanimod (0.1, 0.3, or 1 mg/kg) significantly improved overall kinematic gait score vs. vehicle in cuprizone-treated mice. Statistical comparisons were based on unpaired t-tests of vehicle vs. naïve or treatment vs. vehicle.

Ozanimod and compound (2-R) are neuroprotective in the cuprizone-induced mouse model demonstrating a reduction in swollen and transected axons as a readout of neuronal damage (Vehicle=121±10.8, compound 2-R=32±5.1 SMI-32$^+$ axons per 250,000 μm$^2$ field, p<0.0001) (see, FIG. 1). Furthermore, 1 mg/kg compound 2-S treatment reduced the plasma biomarker NfL (Vehicle=258±49.1 pg/ml, compound (2-S)=127±12.2 pg/ml, p<0.001). In a second study, ozanimod improved kinematic gait in cuprizone-induced demyelinated mice (see, FIG. 2 and FIG. 3), demonstrating an improved functional outcome with ozanimod. In primary rodent astrocytes ozanimod directly activated ERK and AKT signaling pathways and attenuated the release of pro-inflammatory cytokines, including IL-1β, TNFα, IL-6, and KC/GRO induced by LPS activation.

Accordingly, ozanimod and compound (2-R) display neuroprotective characteristics through direct CNS activity, as demonstrated by reduced axonal breaks in the cuprizone mouse model, and improved functional capabilities following cuprizone-induced demyelination. This neuroprotective effect may be due in part by the compounds direct activity on astrocytes by attenuating the cells inflammatory response to a perturbed environment and thus maintaining a more optimal milieu for neuronal survival.

Example 3

Preservation of Brain Volume

As mentioned above, ozanimod is in clinical development for treatment of relapsing multiple sclerosis (RMS). Brain volume loss (BVL) correlates with and predicts disability and is thought to be a marker of long-term disease progression and cognitive impairment. Accordingly, reducing BVL is an important treatment goal. In this example, BVL results are reported from two similarly-designed phase 3 RMS studies.

SUNBEAM (N=1346) and RADIANCE Part B (N=1320) were randomised, double-blind, double-dummy, active-controlled, parallel-group studies of the efficacy (primary outcome annualised relapse rate) and safety of once-daily ozanimod 1 mg or 0.5 mg vs intramuscular interferon beta-1a (IFNβ-1a) 30 μg for ≥12 months (m) (SUNBEAM) or 24 m (RADIANCE). BVL was evaluated using the Jacobian integration method to assess changes in normalised whole brain, cortical grey matter, and thalamic volumes. Rank analysis of covariance was performed with treatment effects reported as percent reductions in median percent BVL from baseline.

Baseline brain volumes were similar across treatment groups.

Ozanimod 1 mg and 0.5 mg both demonstrated slowing of whole BVL vs IFN: 32.5% (p<0.0001) and 12.3% (p=0.0615), respectively, in SUNBEAM (12 m) and 26.6% (p<0.0001) and 24.5% (p=0.0001) vs IFN in RADIANCE (24 m).

Ozanimod 1 mg and 0.5 mg both demonstrated slowing of cortical grey matter loss with respect to IFN: 83.8% (p<0.0001) and 61.4% (p<0.0001), respectively, in SUNBEAM (12 m) and 58.3% (p<0.0001) and 55.1% (p<0.0001) in RADIANCE (24 m).

Ozanimod 1 mg and 0.5 mg both demonstrated slowing of thalamic BVL vs IFN: 38.5% (p<0.0001) and 34.3% (p=0.0001), respectively, in SUNBEAM (12 m) and 31.9% (p<0.0001) and 30.1% (p=0.0008) in RADIANCE (24 m).

Ozanimod resulted in significant reductions of BVL in both phase 3 studies as measured by normalised whole, cortical grey, and thalamic brain volumes at 12 and 24 m. The effect of reducing brain volume loss vs IFNβ-1a, combined with significant outcomes on other radiographic measures of disease activity (reduction in gadolinium-enhancing and T2 lesion load) and the known correlations between BVL and disability/cognitive impairment, indicate ozanimod may be beneficial in reducing tissue damage and thus longer-term disease worsening in RMS patients.

Example 4

Inhibition of Monoamine Oxidases

Monoamine oxidases (MAO) are a family of mitochondrial membrane bound enzymes that catalyze the oxidative deamination of monoamines, including neurotransmitters, such as dopamine, norepinephrine, and serotonin. In humans, there are two types of MAOs, MAO-A and MAO-B, which share about 70% amino acid identity and both have a covalently-bound FAD cofactor attached to an enzyme cysteine via the 8α-methylene of the isoalloxazine ring. Both isozymes are found in and outside the CNS. MAO-A metabolizes serotonin, norepinephrine, and dopamine, while MAO-B preferentially oxidizes benzylamine, dopamine and phenylethylamine and only metabolizes norepinephrine and serotonin slowly. Increased MAO-B activity is associated with neurodegenerative diseases, such as Alzheimer's disease, Parkinson's disease, Huntington's disease. MAO-B inhibitors are being evaluated for the treatment of Alzheimer's disease, Parkinson's disease, and Huntington's disease.

Compound 1 and Compound 2-S were evaluated for their ability to inhibit MAO-A and MAO-B. Inhibition of the conversion of kynuramine, a substrate for MAO-A and MAO-B, to 4-hydroxyquinoline was used to assess the inhibitory potential of Compound 1 and Compound 2-S. Recombinant human MAO-A (product number M7316) and MAO-B (product number M7441) expressed in baculovirus infected insect cells were obtained from Sigma-Aldrich, Saint Louis, Mo. USA were used as a source of purified MAOs.

Recombinant MAO-A (0.01 mg/mL, final concentrations) and MAO-B (0.02 mg/mL, final concentration) were diluted to desired concentrations in 100 mM potassium phosphate buffer (pH 7.4) containing 5 mM $MgCl_2$. The diluted protein fractions were preincubated with various concentrations of each test compound at 37° C. for 2 min. The concentrations used were 100, 33, 10, 3.3, 1.0, 0.33 μM and acetonitrile/DMSO as vehicle control for MAO-A and 1.0, 0.3, 0.1, 0.03, 0.01, 0.003 μM and acetonitrile/DMSO as vehicle control for MAO-B. The reaction was started by addition of kynuramine to the incubation mixture. The final concentration of kynuramine was 40 μM for MAO-A and 25 μM for MAO-B. The total incubation volume was 0.250 mL. This concentration was selected to be close to the Km values of MAO-A (Km 42 μM) and MAO-B (Km 26 μM). After 10 min of incubation, aliquots (100 μL) of the reaction mixture were taken and added to 200 μL acetonitrile containing 0.5 μM IS (acetaminophen). The reaction product, 4-hydroxyquinoline was analyzed by LC-MS/MS as described below.

Inhibition of the conversion of kynuramine, a substrate for MAO-A and MAO-B, to 4-hydroxyquinoline was used to assess the time dependent inhibitory potential of Compound 1. The diluted MAO protein fractions were pre incubated with various concentrations of Compound 1 at 37° C. for 2 min and 30 min as described above. The reaction product, 4-hydroxyquinoline was analyzed by LC-MS/MS as described below.

MS characterization and detection of kynuramine and 4-hydroxyquinoline was performed using ABI 4000 Sciex QTrap mass spectrometer utilizing a Turbo Spray. The mass spectrometer was controlled by Analyst v1.6.2. The ESI was operated in a positive ion mode and the experimental parameters were set as follows: ion spray voltage, 2000; source temperature, 550° C.; curtain gas, 20; collision gas, medium ion source gas 1, 55; ion source gas 2, 50. The analytes were introduced into the mass spectrometer using Waters Acquity UPLC system. The liquid chromatography was performed using a Synergi Polar (4 μm particle size, 3×150 mm RP-80A, Phenomenex).

The gradient system was used to separate the analytes with a flow rate of 0.5 ml/min using mobile phase A, water containing 0.1% formic acid and mobile phase B, acetonitrile containing 0.1% formic acid. The gradient started with 95% A and 5% B and held for 0.5 min. It was then progressed to 60% A and 40% B in 2.5 min followed by 5% A and 95% B in 0.5 min. This was held for 1 min and reverted back to initial composition of 95% A and 5% B. The column was allowed to equilibrate for 1 min. The total run time was 6 min. The retention times of 4-hydroxyquinoline and internal standard (acetaminophen) were 4.02 and 3.75 min, respectively. The analytes were monitored using multiple reaction monitoring and the ion transitions (Q1/Q3) were as follows: 4-hydroxyquinoline 146/104 (collision energy, CE was 27; declustering potential, DP, 50, and IS (acetaminophen), 152/110 (collision energy, CE was 27; declustering potential, DP, 50). All data were analyzed using AB Sciex Analyst v1.6.2 software.

Figure 5A:
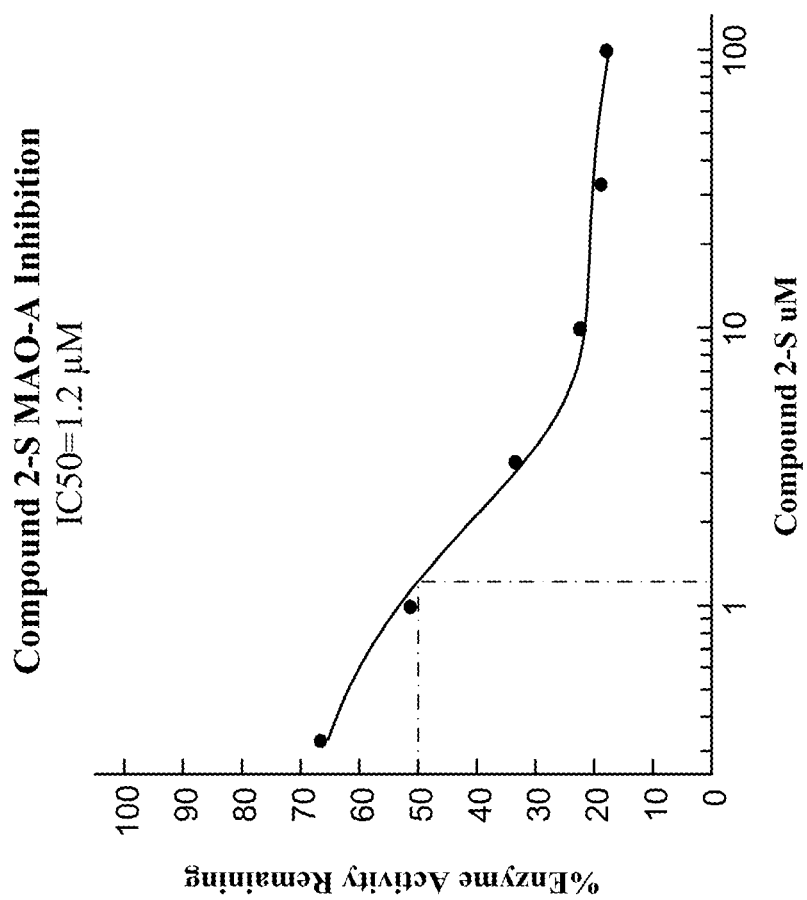
FIGS. 5A-5B are line graphs showing that Compound 2-S has inhibitory activity against MAO-A (FIG. 2A) and MAO-B (FIG. 2B).
Figure 5B:
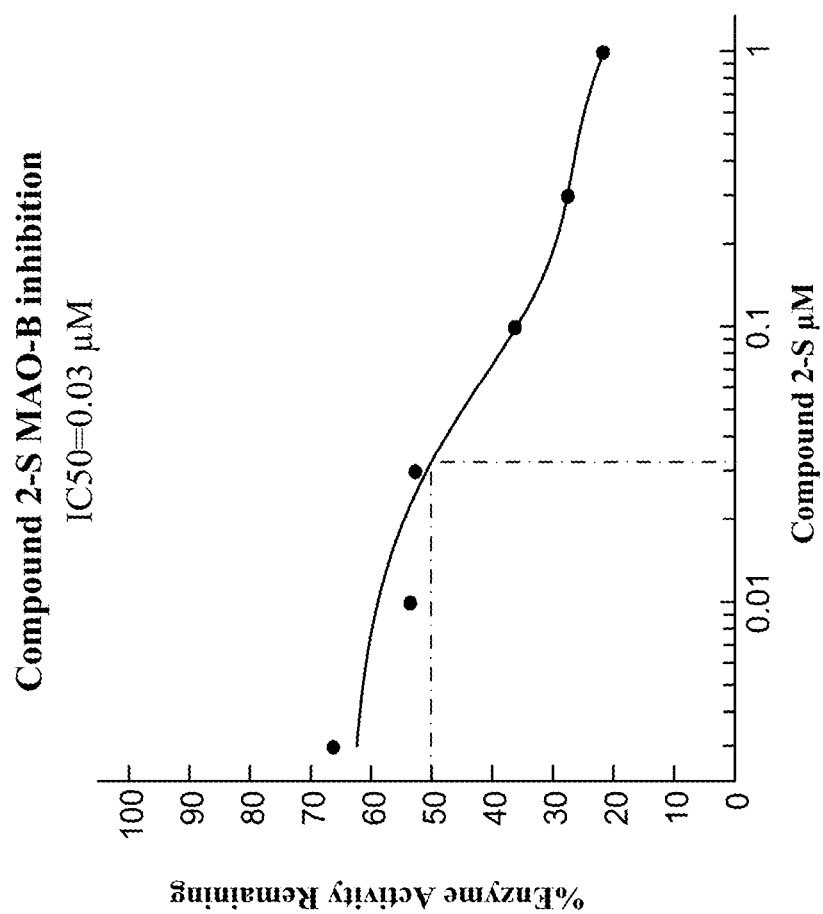
Figure 6A:
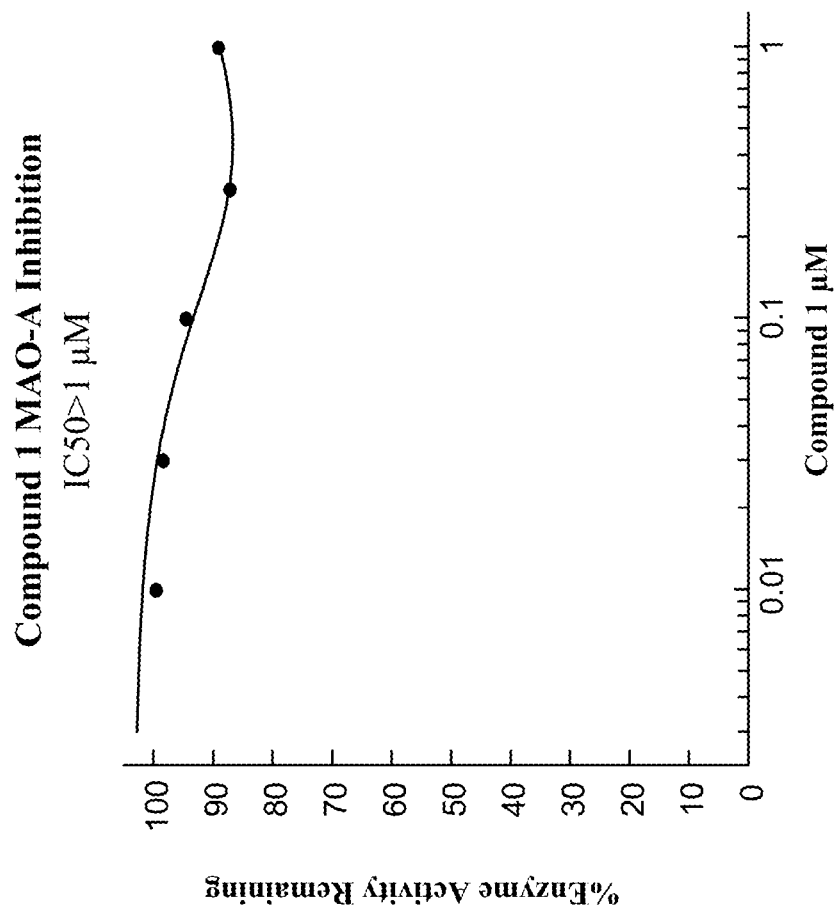
FIGS. 6A-6B are line graphs showing that Compound 1 does not inhibit MAO-A (FIG. 3A) but shows potent inhibition of MAO-B (FIG. 3B).
Figure 6B:
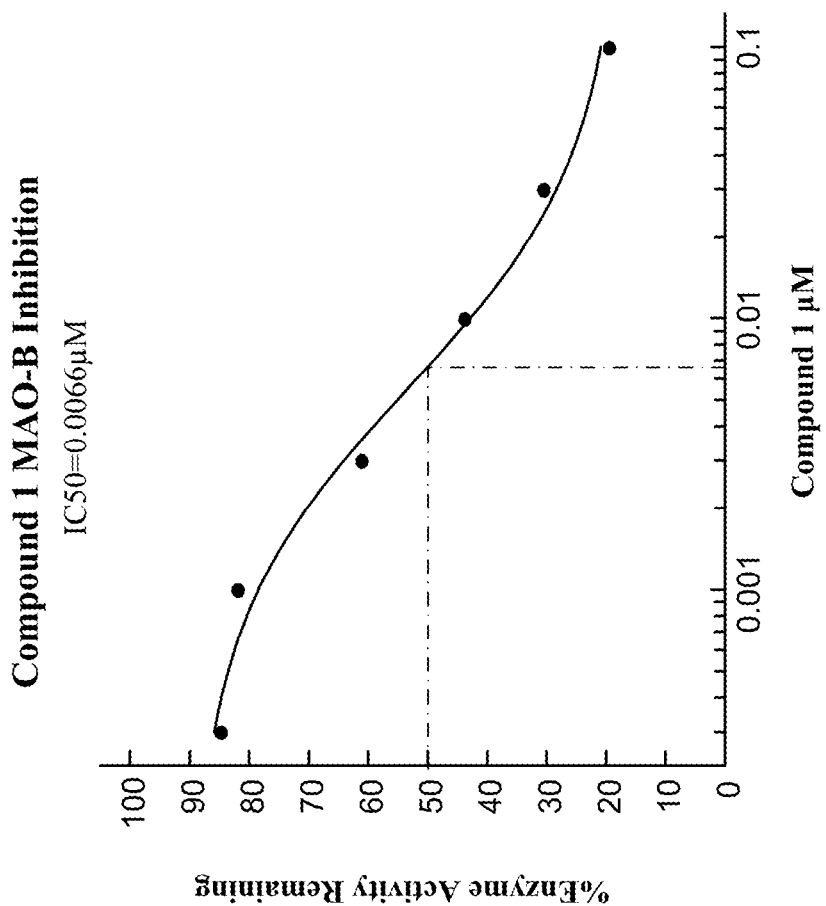

Compound 2-S inhibits both MAO-A (IC50 value of 1.2 µM) and MAO-B (IC50 value of 0.032 µM) (FIGS. 4, 5A-5B). Compound 1 is not an inhibitor of MAO-A but a potent inhibitor of MAO-B with IC50 value of 6.6 nM (FIGS. 4, 6A-6B).

Example 5

Activation of AKT and ERK in Cortical Astrocytes 2-amino-2-[2-(4-octylphenyl)ethyl]-1,3-propanediol (FTY720), also known as fingolimod, is an approved treatment for the relapsing form of multiple sclerosis. In vivo phosphorylation of FTY720 generates a S1P receptor agonist. In vitro treatment of cortical astrocytes with phosphorylated FTY720 (FTY720-P) results in rapid phosphorylation of ERK1/2 and AKT, two enzymes involved in cell survival pathways. In this example, the effect of ozanimod, Compound 1, Compound 3, and FTY720-P (positive control) on rat, mouse, and human cortical astrocytes were assessed in vitro.

Ozanimod, Compound 1, and Compound 3 were synthesized and dissolved in 100% DMSO to 10 mM and stored in single-use aliquots at −80° C. FTY720-P was purchased from Cayman Chemical (Ann Arbor, Mich.) and dissolved in anhydrous DMSO to 0.5 mM and stored in single-use aliquots at −80° C.

For the experiments using rat primary astrocytes, eight-point concentration-response curves were generated for AKT and ERK phosphorylation in primary rat astrocytes cultures in response to a 10-minute treatment with ozanimod (100 nM-46 pM), Compound 3 (10 nM-5 pM), Compound 1 (10 nM-5 pM), or FTY720-P (10 nM-5 pM). Phosphorylation of AKT and ERK was quantified using Meso Scale Discovery assay kits (MSD Mutli-Spot Phopho-AKT (Ser473) Assay Kit and MSD Multi-Spot MAP Kinase Phosphoprotein Assay Whole Cell Lysate Kit) and imaging platform. AKT and ERK phosphorylation within treated astrocytes were assessed as the mean change in signal intensity compared to DMSO vehicle and the half maximal effective concentration (EC50) was determined using non-linear regression.

Embryonic day18 (E18) rat cortices were purchased from BrainBits LLC. (Springfield, Ill.) and were cultured according to the supplier's protocol. Briefly, cortices were incubated at 37° C. for 10 minutes in activated papain solution before trituration in hibernation medium containing B27 supplement using a modified siliconized glass Pasteur pipette. The cell suspension was centrifuged at 1100×g for 1 minute at room temperature (RT). The cell pellet was then resuspended in NbAstro medium (BrainBits LLC.) and the live cell density was assessed using a cell counter. Primary cells were plated at a density of 7500 cells/cm2 in T75 tissue culture flasks coated with poly-D-lysine (PDL) in a total volume of 12 mL of NbAstro media, and incubated for 10-14 days at 37° C. 5% $CO_2$. After 10-14 days, primary astrocytes in passage 0 (P0) that had reached confluency in the T75 flasks were detached using TrypLE detachment reagent, pelleted at 300×g, and plated into poly-d-lysine coated T225 flasks in 20 mL of NbAstro media, and incubated for another 7 days at 37° C. 5% $CO_2$. After 7 days, primary P1 astrocytes in confluent T225 flasks were detached using TrypLE detachment reagent, pelleted at 300×g, and plated intopoly-d-lysine coated 96-well plates at 10,000 cells per well in 200 µL of NbAstro media, and incubated for 7 days at 37° C. 5% $CO_2$. After 7 days, P2 primary astrocytes were utilized for pAKT and pERK assays.

The pAKT (phosphorylated AKT) assay was performed according to the manufacturer's protocol. Briefly, MSD pAKT plates were blocked for 1-2 hours by adding 150 µL of blocker A prepared in 1× Tris wash buffer. Following blocking, plates were washed 3 times using 1× Tris wash buffer and the astrocytic lysates (45 µL/well) added. Plates were sealed with adhesive plate seal and incubated for 1 hr at RT on shaker. After incubation, plates were washed three times with 150 µL of 1× Tris wash buffer and antibody solution (25 µL/well) was added. Plates were sealed with adhesive plate seal and incubated for 1 hr at RT on shaker. Following antibody incubation, plates were washed three times with 150 µL of 1× Tris wash buffer and 1× read buffer (150 µL/well) was added. Finally, plates were read in the MSD imager platform to assess pAKT levels.

The pERK (phosphorylated ERK)/pMAPkinase assay was performed according to the manufacturer's protocol. Briefly, MSD pERK/pMAPkinase plates were blocked for 1-2 hours by adding 150 µL of blocker A prepared in 1× Tris wash buffer. Following blocking, plates were washed 3 times using 1× Tris wash buffer and the astrocytic lysates (45 µl/well) added. Plates were sealed with adhesive plate seal and incubated for either 3-hours at RT or overnight at 4° C. with shaking. After incubation, plates were washed three times with 150 µL of 1× Tris wash buffer and the antibody solution (25 µL/well) was added. Plates were sealed with adhesive plate seal and incubated for 1 hr at RT with shaking. Following antibody incubation, plates were washed three times with 150 µL of 1× Tris wash buffer and 1× read buffer (150 µL/well) was added. Finally, the plates were read in the MSD imager platform to assess the pERK levels.

AKT and ERK phosphorylation data were analyzed by non-linear regression (GraphPad Prism, version 6) to determine the $EC_{50}$ values.

Figure 8:
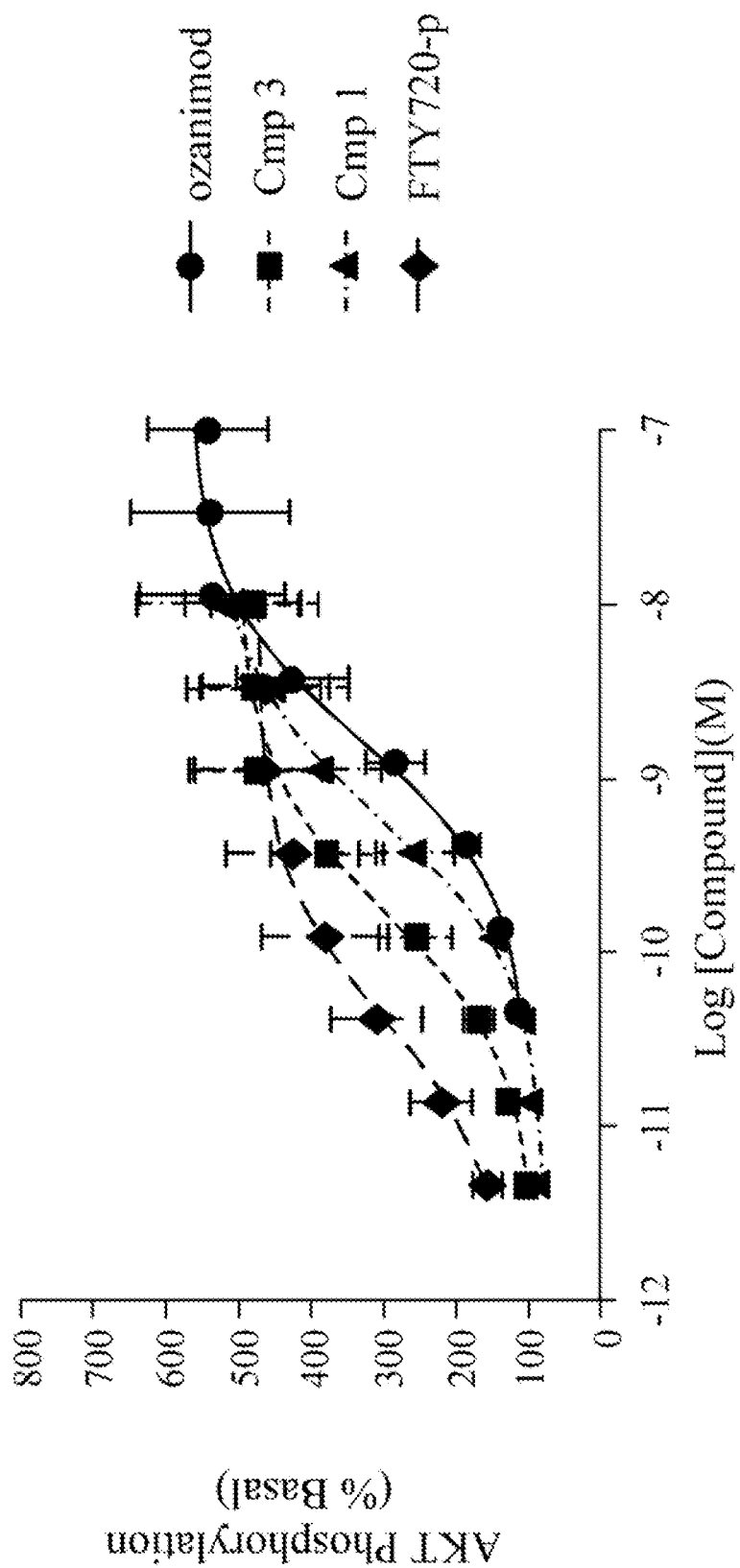
FIG. 8 shows concentration response analysis of AKT phosphorylation in primary rat astrocytes in response to ozanimod, Compound 3, Compound 1, and FTY720-P. The data shown are the mean and standard error of the mean levels of AKT phosphorylation generated in primary rat astrocytes in response to a 10-minute exposure to test compound in n=4 independent experiments.
Figure 9:
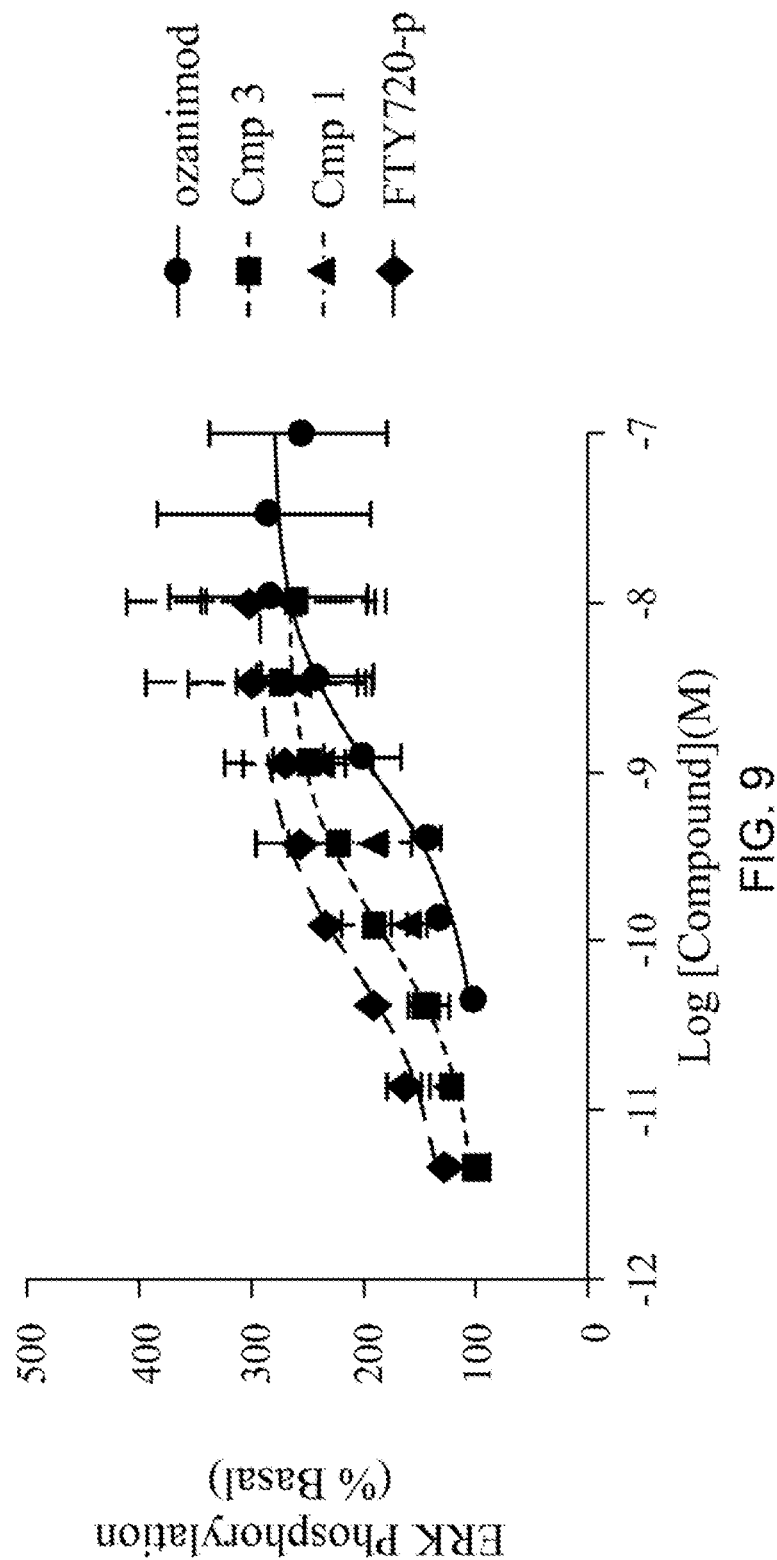
FIG. 9 shows concentration response analysis of ERK phosphorylation in primary rat astrocytes in response to ozanimod, Compound 3, Compound 1, and FTY720-P. The data shown are the mean and standard error of the mean levels of ERK phosphorylation generated in primary rat astrocytes in response to a 10-minute exposure to test compound in n=3 independent experiments.

Mean concentration-response data following a 10-minute stimulation with the test compounds are shown for AKT phosphorylation in FIG. 8, and for ERK phosphorylation in FIG. 9. Mean EC50 values for both readouts are summarized in FIG. 7. Ozanimod, Compound 3, Compound 1, and the positive control, FTY720-P elicited concentration-dependent phosphorylation of AKT with $EC_{50}$ values of 2.03, 0.23, 0.66, and 0.17 nM, respectively. In a similar fashion, oznaimod, Compound 3 Compound 1, and the positive control, FTY720-P induced concentration-dependent phosphorylation of ERK with $EC_{50}$ values of 0.80, 0.11, 0.29, and 0.16 nM, respectively. Ozanimod, Compound 3, and Compound 1 are potent activators of AKT and ERK signaling pathways in primary rat cortical astrocytes. Additionally, FTY720-P also phosphorylated the proteins at similar concentrations.

For the experiments using mouse and human primary astrocytes, ten-point concentration-response curves (90 nM-4.57 pM or 30 nM-1.52 pM) were generated for AKT and/or ERK phosphorylation in primary human and mouse cortical astrocytic cultures in response to a 10-minute treatment with ozanimod, Compound 3, Compound 1, or FTY720-P. AKT and ERK phosphorylation were quantified using AlphaLISA SureFire Ultra Assay kits and the EnVision Plate Reader. AKT and ERK phosphorylation within treated astrocytes were expressed as the mean change in signal intensity compared to the dimethyl sulfoxide (DMSO) vehicle and the half maximal effective concentration (EC50) was determined using non-linear regression.

Primary human astrocytes were purchased from ScienCell Research Laboratories, Inc. and cultured according to the supplier's protocol. The astrocytes were obtained from the human cerebral cortex, cryopreserved at passage one, and delivered frozen. The frozen vials of cells were gently thawed in a 37° C. water bath. Once the contents of the vial were completely thawed, the cell solution was dispensed into a poly-L-lysine (PLL) coated T75 tissue culture flask with 16 mL of human Astrocyte Media, (ScienCell Research Laboratories, Inc.) and incubated at 37° C. 5% $CO_2$. Once the human astrocytes had reached confluency in the T75 flask, they were detached using trypsin/EDTA 0.25%, pelleted at 300×g, split into two PLL coated T225 tissue culture flasks in 40 mL of astrocyte media, and incubated at 37° C. 5% $CO_2$. Once the astrocytes reached confluency in the T225 flasks, they were detached using trypsin/EDTA 0.25% solution, pelleted at 300×g, plated into poly-D-lysine (PDL) coated 96-well plates at a density of 10,000 cells per well in 200 µL human Astrocyte Media, and incubated at 37° C. 5% $CO_2$. Half of the media was replenished every 3-4 days. After 5-7 days of incubation, the P2 human astrocyte plates were utilized for the pERK and pAKT assays.

Timed pregnant (E16) C57BL/6J female mice arrive to the test facility on a weekly basis and were housed and cared for according to appropriate protocols for this model. Primary mouse cortical astrocytes are harvested from P0-P2 pups. The newly born animals were deeply anesthetized on ice, decapitated, and the brains were rapidly removed and stored in ice-cold NbAstro media (BrainBits, LLC). Cells were dissociated from freshly dissected cortices by mechanical disruption in the presence of trypsin and DNase. Cells were put into a PDL coated T75 tissue culture flask containing 16 mL NbAstro Media and incubated at 37° C. 5% $CO_2$. Once the mouse astrocytes had reached confluency in the T75 flask, they were detached using TripLE detachment reagent, pelleted at 300×g, expanded into two T225 PDL coated tissue culture flasks containing 40 mL of NbAstro and incubated at 37° C. 5% $CO_2$. Once the astrocytes reached confluency in the T225 flasks they were detached using TrypLE detachment reagent, pelleted at 300×g, plated into PDL coated 96-well plates at a density of 10,000 cells per well in 200 µL NbAstro and incubated at 37° C. 5% $CO_2$. Half of the media was replenished every 3-4 days. After 5-7 days of incubation, the P2 mouse astrocyte plates were utilized for the pERK and pAKT assays.

Cell lysis and detection of pAKT were performed according to the PerkinElmer AlphaLISA SureFire Ultra pAKT1/2/3 (Ser273) assay protocol. Astrocytes were lysed in the 96-well plate following a 10 minute incubation with compounds with shaking at room temperature (RT). The astrocytic lysates (10 µL/well) were transferred into a 384-well OptiPlate. As specified by the assay protocol, an acceptor bead mix and a donor bead mix (5 µL/well for each) were added to the plate under subdued light. Plates were sealed with adhesive plate seals and incubated in the dark for 2 hours at RT. The plates were read on the EnVision Plate Reader to assess the pAKT levels.

Cell lysis and detection of pERK were performed according to the PerkinElmer AlphaLISA SureFire Ultra p-ERK1/2 (Thr202/TYR 204) assay protocol. Astrocytes were lysed in the 96-well plate following a 10 minute incubation with compounds with shaking at RT. The astrocytic lysates (10 µL/well) were transferred into a 384-well OptiPlate. As specified by the assay protocol, an acceptor bead mix and a donor bead mix (5 µL/well for each) were added to the plate under subdued light. Plates were sealed with adhesive plate seals and incubated in the dark for 2 hours at RT. The plates were read on the EnVision Plate Reader to assess the pERK levels.

The AKT and ERK phosphorylation data, collected by a Perkin Elmer EnVision Microplate Reader, was analyzed by non-linear regression (GraphPad Prism, version 7.03) to determine the $EC_{50}$ values.

Figure 11:
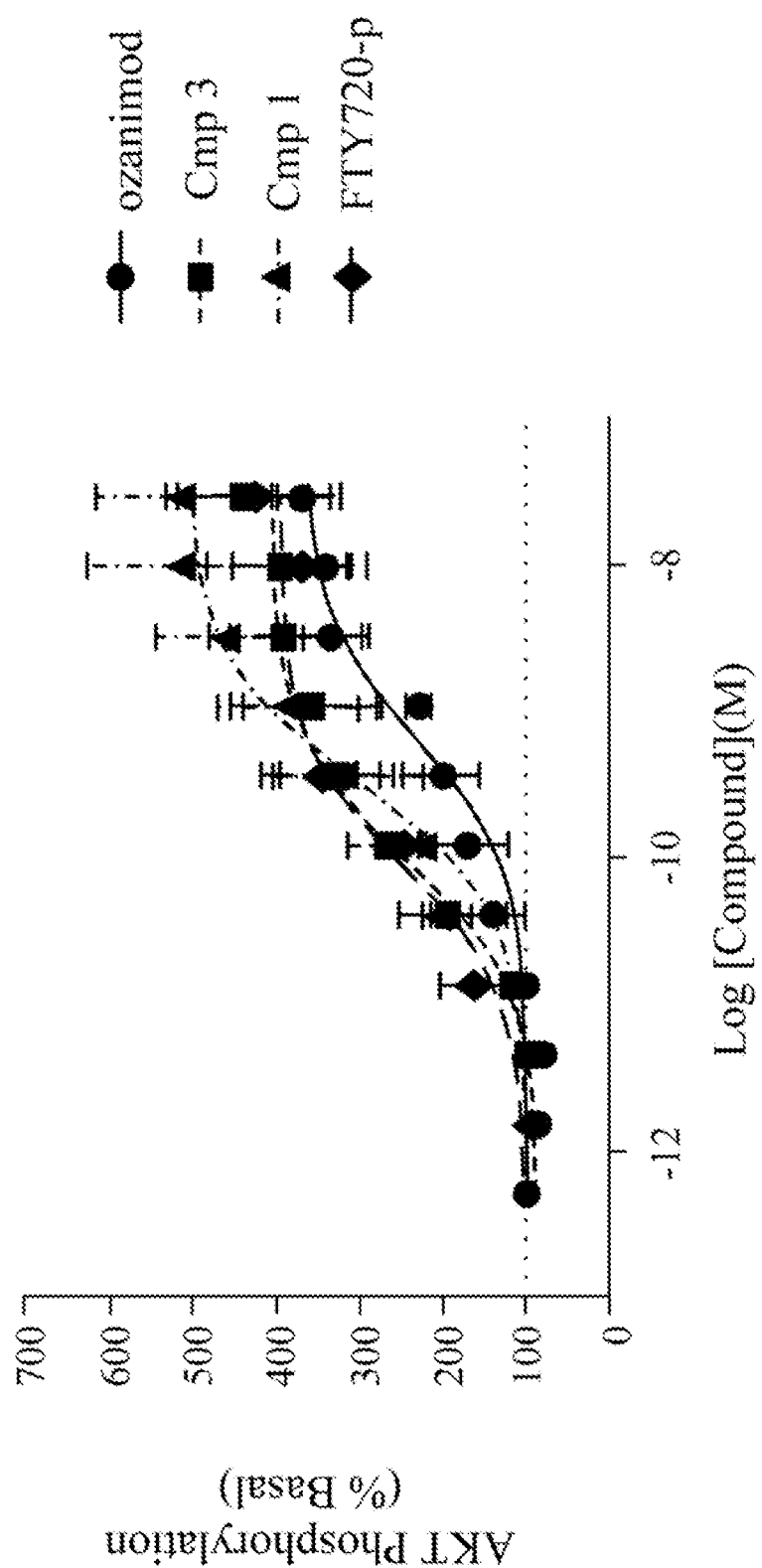
FIG. 11 shows concentration response analysis of AKT phosphorylation in primary mouse astrocytes in response to ozanimod, Compound 3, and Compound 1, and FTY720-P. The data shown are the mean and standard error of the mean levels of AKT phosphorylation generated in primary mouse astrocytes in response to a 10-minute exposure to test compound in n=3 independent experiments.
Figure 12:
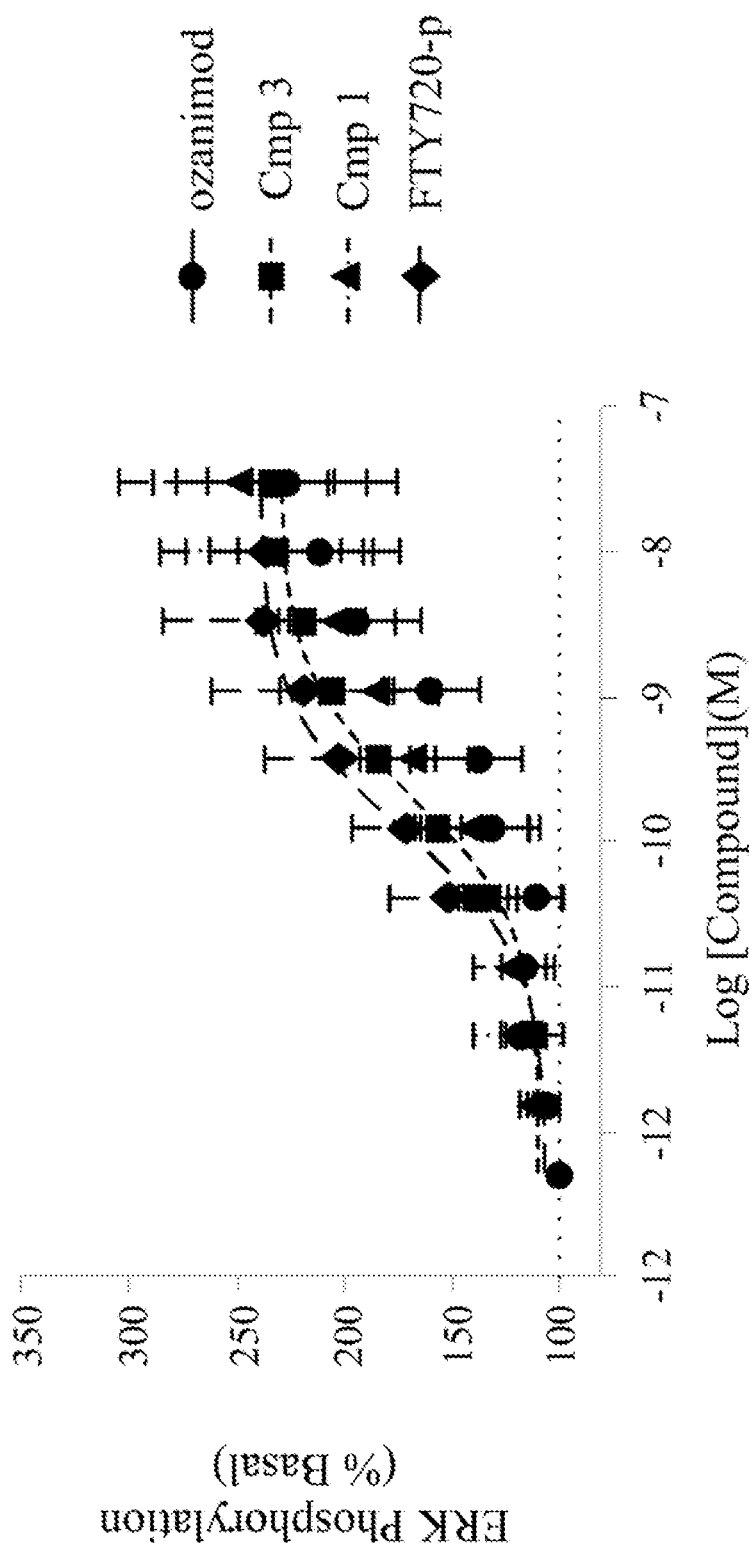
FIG. 12 shows concentration response analysis of ERK phosphorylation in primary mouse astrocytes in response to ozanimod, Compound 3, and Compound 1, and FTY720-P. The data shown are the mean and standard error of the mean levels of ERK phosphorylation generated in primary mouse astrocytes in response to a 10-minute exposure to test compound in n=3 independent experiments.
Figure 13:
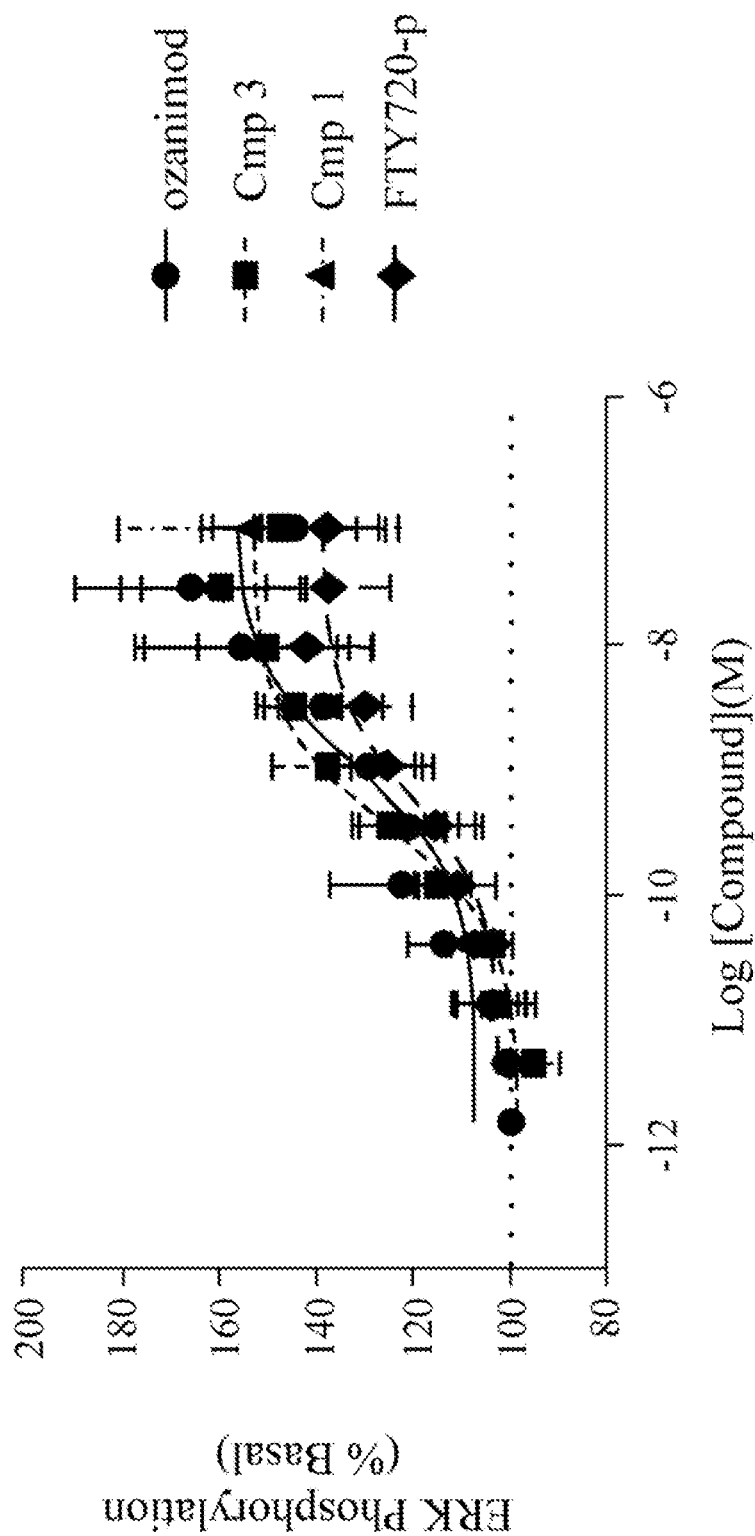
FIG. 13 shows concentration response analysis of ERK phosphorylation in primary human astrocytes in response to ozanimod, Compound 3, and Compound 1, and FTY720-P. The data shown are the mean and standard error of the mean levels of ERK phosphorylation generated in primary human astrocytes in response to a 10-minute exposure to test compound in n=3-5 independent experiments.

Mean concentration-response data following a 10-minute stimulation with the test compounds are shown for AKT phosphorylation in mouse astrocytes in FIG. 11. Mean concentration response data following a 10-minute stimulation with the test compounds are shown for ERK phosphorylation in mouse astrocytes FIG. 12 and in human astrocytes in FIG. 13. Mean $EC_{50}$ values for both readouts in both species are summarized in FIG. 10. Ozanimod, Compound 3, Compound 1, and the positive control, FTY720-P elicited concentration-dependent phosphorylation of AKT in mouse astrocytes with $EC_{50}$ values of 0.90, 0.13, 0.49, and 0.09 nM, respectively. In a similar fashion, ozanimod, Compound 3, Compound 1, and the positive control, FTY720-P induced concentration-dependent phosphorylation of ERK in mouse astrocytes with EC50 values of 2.42, 0.0.23, 0.87, and 0.14 nM, respectively, and in human astrocytes with $EC_{50}$ values of 1.93, 0.50, 2.12, and 0.73 nM, respectively. Ozanimod, Compound 3, and Compound 1 are potent activators of AKT and/or ERK signaling pathways in primary mouse and human cortical astrocytes. Notably the potency of the ERK responses were similar for ozanimod, Compound 3, and Compound 1 between mouse and human, demonstrating consistent activity across both species and with the rat AKT and ERK potencies detailed above. FTY720-P also demonstrated potent activation of both AKT and/or ERK in mouse and human.

U.S. Provisional Patent Application No. 62/502,909, filed May 8, 2017 and Application No. 62/544,467, filed on Aug. 11, 2017 to which the present application claims priority, is hereby incorporated herein by reference in their entirety.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, are incorporated herein by reference, in their entirety. Aspects of the embodiments can be modified, if necessary to employ concepts of the various patents, applications and publications to provide yet further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled.

We claim:

1. A method of treating a patient with a disease selected from the group consisting of Parkinson's disease, amyotrophic lateral sclerosis, Alzheimer's disease, and Rett syndrome, the method comprising administering to the patient a therapeutically effective amount of a compound having one of the following structures:

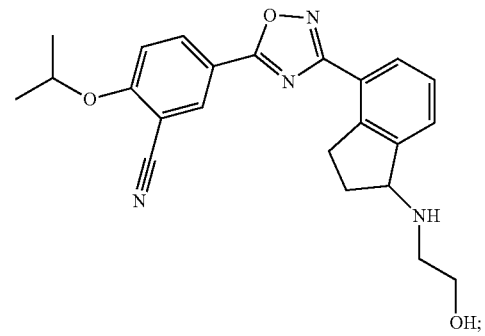 [SMILES: CC(C)Oc1ccc(-c2nc(-c3cccc4c3CCC4NCCO)no2)cc1C#N]

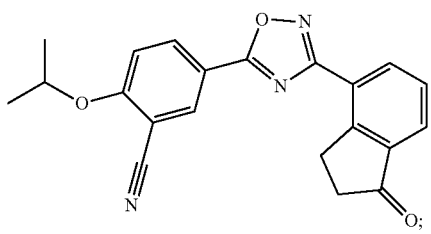

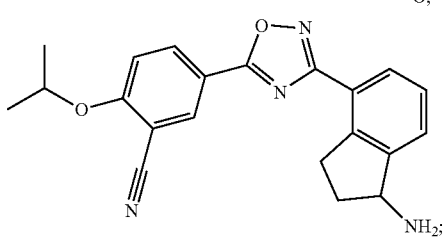

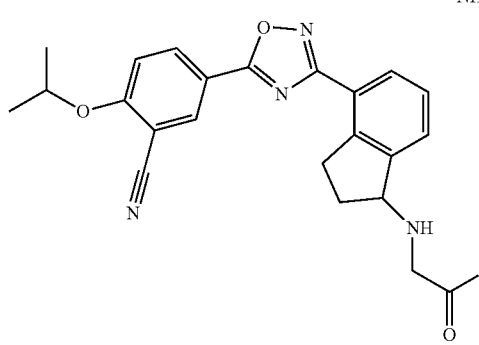

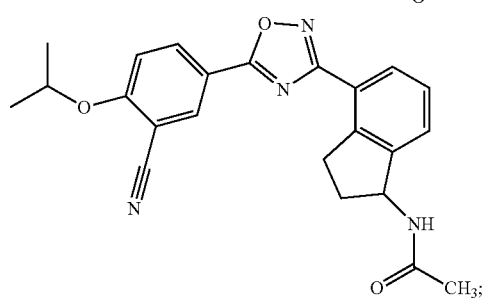

or a pharmaceutically acceptable salt, stereoisomer, homolog, hydrate or solvate thereof.

2. The method of claim 1, wherein treating the patient with the therapeutically effective amount of the compound is evidenced by a reduction in spinal cord inflammation in the patient.

3. The method of claim 1, wherein treating the patient with the therapeutically effective amount of the compound is evidenced by a reduction in spinal cord axial demyelination.

4. The method of claim 1, wherein treating the patient with the therapeutically effective amount of the compound is evidenced by a reduction in T cell expansion, a decrease in monocyte infiltration into the spinal cord, limiting microglia expansion into the spinal cord, or any combination thereof.

5. The method of claim 1, wherein treating the patient with the therapeutically effective amount of the compound is evidenced by a reduction in brain volume loss.

6. The method of claim 1, wherein treating the patient with the therapeutically effective amount of the compound is evidenced by a reduction in MAO-B activity.

7. The method of claim 1, wherein the compound has the following structure:

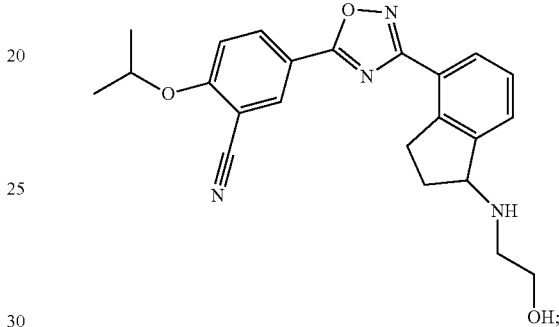

or a pharmaceutically acceptable salt, stereoisomer, homolog, hydrate or solvate thereof.

8. The method of claim 7, wherein the compound is ozanimod.

9. The method of claim 1, wherein the compound has the following structure:

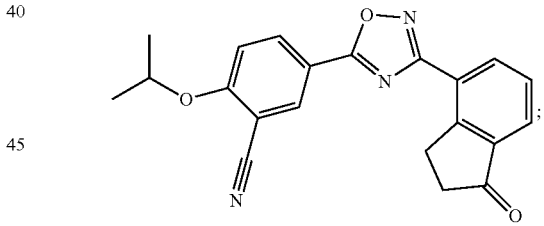

or a pharmaceutically acceptable salt, homolog, hydrate or solvate thereof.

10. The method of claim 1, wherein the compound has the following structure:

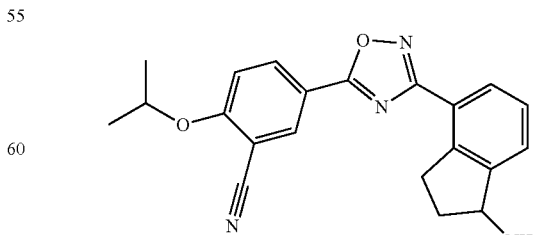

or a pharmaceutically acceptable salt, stereoisomer, homolog, hydrate or solvate thereof.

11. The method of claim 1, wherein the compound has the following structure:
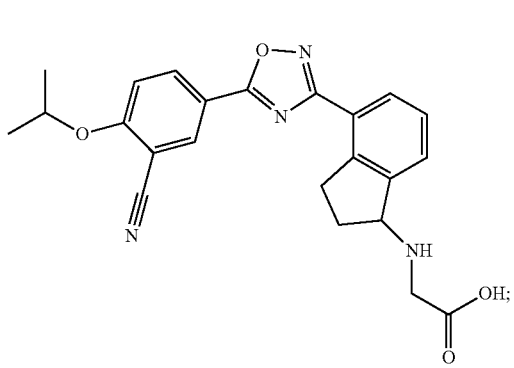 [SMILES: CC(C)Oc1ccc(-c2nc(-c3cccc4c3CCC4NCC(=O)O)no2)cc1C#N]
or a pharmaceutically acceptable salt, stereoisomer, homolog, hydrate or solvate thereof.
12. The method of claim 1, wherein the compound has the following structure:
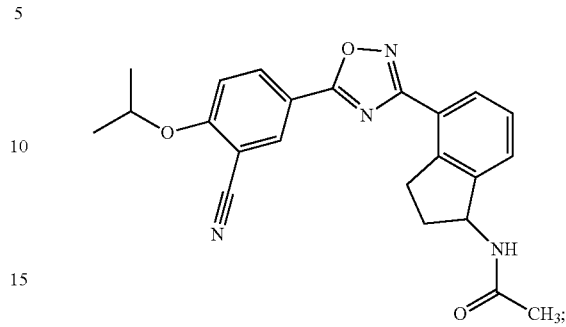
or a pharmaceutically acceptable salt, stereoisomer, homolog, hydrate or solvate thereof.
* * * * *